United States Patent
Hirai et al.

(10) Patent No.: US 9,675,818 B2
(45) Date of Patent: Jun. 13, 2017

(54) APPARATUS, METHOD AND SYSTEM FOR MEDICAL IMAGE-BASED RADIOTHERAPY PLANNING

(71) Applicant: KABUSHIKI KAISHA TOSHIBA, Tokyo (JP)

(72) Inventors: Ryusuke Hirai, Tokyo-to (JP); Yukinobu Sakata, Kawasaki (JP); Yasunori Taguchi, Kawasaki (JP); Kyoka Sugiura, Kawasaki (JP); Atsushi Yaguchi, Kawasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 14/337,649

(22) Filed: Jul. 22, 2014

(65) Prior Publication Data
US 2015/0045605 A1 Feb. 12, 2015

(30) Foreign Application Priority Data
Aug. 6, 2013 (JP) .................. 2013-163425

(51) Int. Cl.
*G06K 9/00* (2006.01)
*A61N 5/10* (2006.01)
(Continued)

(52) U.S. Cl.
CPC ............ *A61N 5/103* (2013.01); *A61B 6/0457* (2013.01); *A61B 6/5223* (2013.01); *A61B 6/5264* (2013.01); *A61N 2005/1062* (2013.01)

(58) Field of Classification Search
None
See application file for complete search history.

(56) References Cited

U.S. PATENT DOCUMENTS 6,516,046 B1 * 2/2003 Frohlich .................. A61B 6/04
378/205
7,035,450 B1 4/2006 Muller et al.
(Continued)

FOREIGN PATENT DOCUMENTS

JP 2004-105746 4/2004
JP 2006-239254 9/2006
(Continued)

OTHER PUBLICATIONS

G. Forlani et al. "Target detection and epipolar geometry for image orientation in close-range photogrammetry," Int'l Archives of Photogrammetry and Remote Sensing, vol. XXXI, Part B5, 1996, pp. 518-523.*
(Continued)

*Primary Examiner* — Vu Le
*Assistant Examiner* — Samah Beg
(74) *Attorney, Agent, or Firm* — Nixon & Vanderhye, P.C.

(57) ABSTRACT

A medical image processing apparatus includes: a receiver which receives target image data that is including a first perspective image and a second perspective image, photographing an object from different directions; a first acquirer which acquires positional information of a specified point on the first perspective image; a second acquirer which acquires positional information of a candidate point on the second perspective image, the candidate point corresponding to the specified point; and a generator which generates a first enlarged image obtained by enlarging a part of the first perspective image neighboring the specified point and a second enlarged image obtained by enlarging a part of the second perspective image neighboring the candidate point.

15 Claims, 19 Drawing Sheets

(51) Int. Cl.
*A61B 6/04* (2006.01)
*A61B 6/00* (2006.01)

(56) References Cited

U.S. PATENT DOCUMENTS

| | | | |
|---|---|---|---|
| 8,077,936 B2* | 12/2011 | Wang | A61N 5/103 382/128 |
| 2002/0024516 A1* | 2/2002 | Chen | G06T 7/0075 345/419 |
| 2003/0137508 A1* | 7/2003 | Appel | G06T 7/0028 345/419 |
| 2003/0212327 A1* | 11/2003 | Wang | A61B 6/463 600/437 |
| 2005/0002559 A1* | 1/2005 | Terauchi | G06T 7/0075 382/154 |
| 2005/0203373 A1* | 9/2005 | Boese | A61B 6/481 600/407 |
| 2006/0210147 A1 | 9/2006 | Sakaguchi | |
| 2006/0241387 A1 | 10/2006 | Nagamine et al. | |
| 2006/0269165 A1* | 11/2006 | Viswanathan | G06T 5/50 382/293 |
| 2007/0043286 A1* | 2/2007 | Lu | A61N 5/103 600/407 |
| 2007/0237295 A1* | 10/2007 | Gundel | A61B 6/032 378/62 |
| 2008/0137934 A1 | 6/2008 | Sakaguchi et al. | |
| 2008/0234570 A1 | 9/2008 | Gerard et al. | |
| 2008/0240349 A1* | 10/2008 | Herrmann | A61N 5/1049 378/65 |
| 2010/0056908 A1* | 3/2010 | Giller | A61B 19/50 600/426 |
| 2010/0067739 A1* | 3/2010 | Mostafavi | G06T 7/2086 382/103 |
| 2010/0189218 A1 | 7/2010 | Sakaguchi et al. | |
| 2011/0107270 A1* | 5/2011 | Wang | G06F 19/3437 715/850 |
| 2011/0210261 A1* | 9/2011 | Maurer, Jr. | A61N 5/10 250/393 |
| 2012/0069968 A1* | 3/2012 | Core | A61N 5/1049 378/206 |
| 2012/0154446 A1* | 6/2012 | Adams | G06T 3/0081 345/661 |
| 2012/0296202 A1 | 11/2012 | Mountney et al. | |
| 2012/0314919 A1* | 12/2012 | Sparks | G06F 19/321 382/128 |
| 2013/0178690 A1* | 7/2013 | Masumoto | A61N 5/1037 600/1 |
| 2015/0154752 A1* | 6/2015 | Hirai | G06T 7/0026 382/132 |
| 2015/0154757 A1* | 6/2015 | Sakata | G06T 11/60 600/1 |
| 2015/0269766 A1* | 9/2015 | Kobayashi | A61B 6/502 345/419 |
| 2015/0279111 A1* | 10/2015 | Sugiura | G06T 19/006 345/424 |
| 2015/0287189 A1* | 10/2015 | Hirai | G06T 7/0012 382/131 |

FOREIGN PATENT DOCUMENTS

| | | |
|---|---|---|
| JP | 2006-247268 | 9/2006 |
| JP | 2007-526066 | 9/2007 |
| JP | 2008-142543 | 6/2008 |
| JP | 2011-212130 | 10/2011 |

OTHER PUBLICATIONS

C. Messom and A. Barczak. "Fast and Efficient Rotated Haar-like Features using Rotated Integral Images," Australian Conference on Robotics and Automation, 2006.*

R. Niese et al. "A New Multi-camera Based Facial Expression Analysis Concept," ICIAR 2012, Part II, LNCS 7325, pp. 64-71.*

Walker, K. et al. "Correspondence Using Distinct Points Based on Image Invariants." BMVC (1997), pp. 1-10.*

Office Action mailed Feb. 16, 2016 in counterpart Chinese Patent Application No. 201410382724.7.

Niese, R. et al., "A New Multi-camera Based Facial Expression Analysis Concept." Springer-verlag Berlin Heidelberg, 2012, pp. 64-71.

Messom, C. et al., "Stream processing for fast and efficient rotated Haar-like features using rotated integral images." International Journal of Intelligent Systems Technologies and Applications, No. 1, vol. 7, 2009, pp. 1-18.

English-language machine translation of JP 2004-105746.

* cited by examiner

AT THE TIME OF THERAPEUTIC PLANNING $V_1(X_1, Y_1, Z_1)$

AT THE TIME OF THERAPY

RADIOACTIVE RAY $V_1(X_1, Y_1, Z_1)$ $V_2(X_2, Y_2, Z_2)$

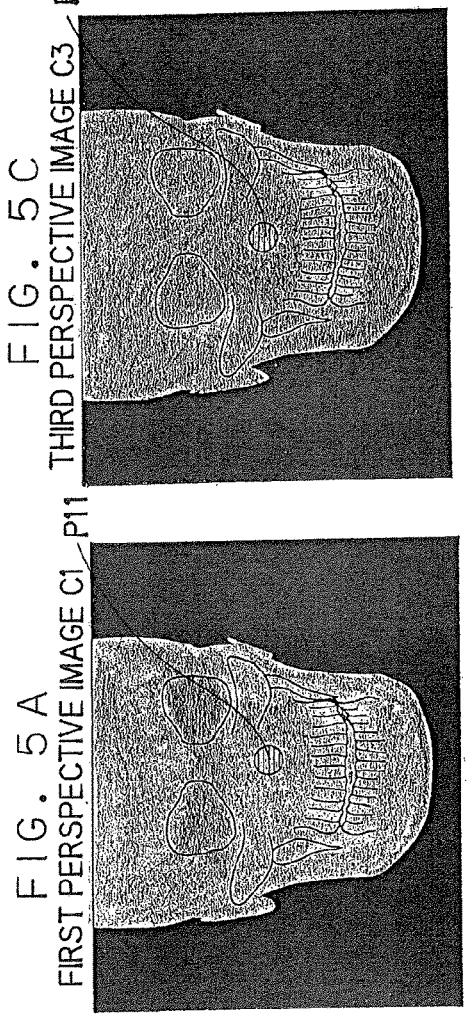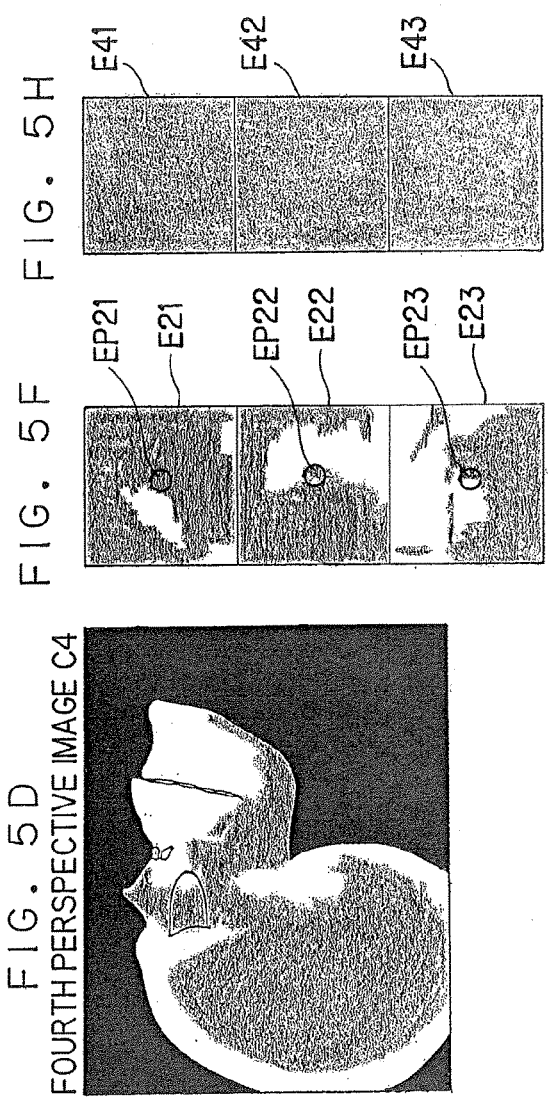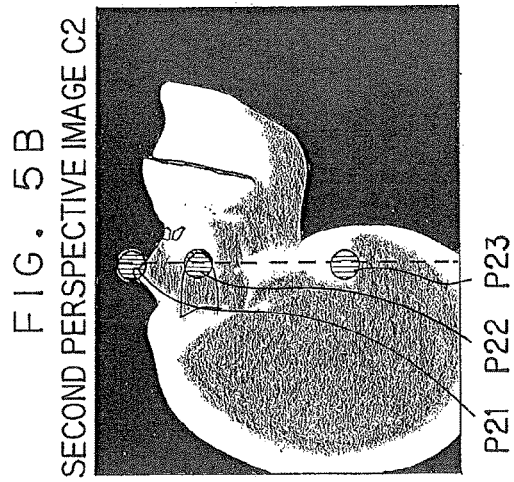
FIG. 5A FIRST PERSPECTIVE IMAGE C1, P11
FIG. 5B SECOND PERSPECTIVE IMAGE C2, P21 P22 P23
FIG. 5C THIRD PERSPECTIVE IMAGE C3, P31
FIG. 5D FOURTH PERSPECTIVE IMAGE C4
FIG. 5E ENLARGED IMAGE E11, EP11
FIG. 5F EP21 E21, EP22 E22, EP23 E23
FIG. 5G ENLARGED IMAGE E31, EP31
FIG. 5H E41, E42, E43

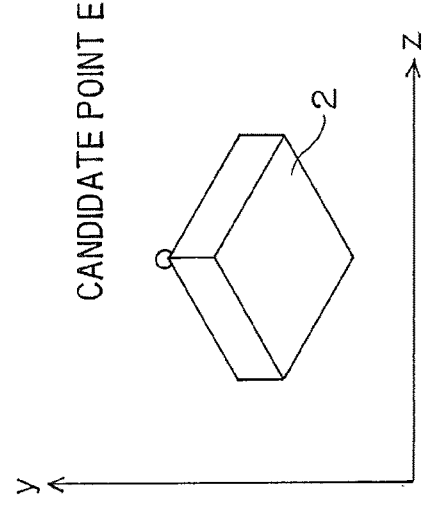
FIG. 11A
FIRST PROJECTING SURFACE F1
SPECIFIED POINT P
FIG. 11B
SECOND PROJECTING SURFACE F2
CANDIDATE POINT EP
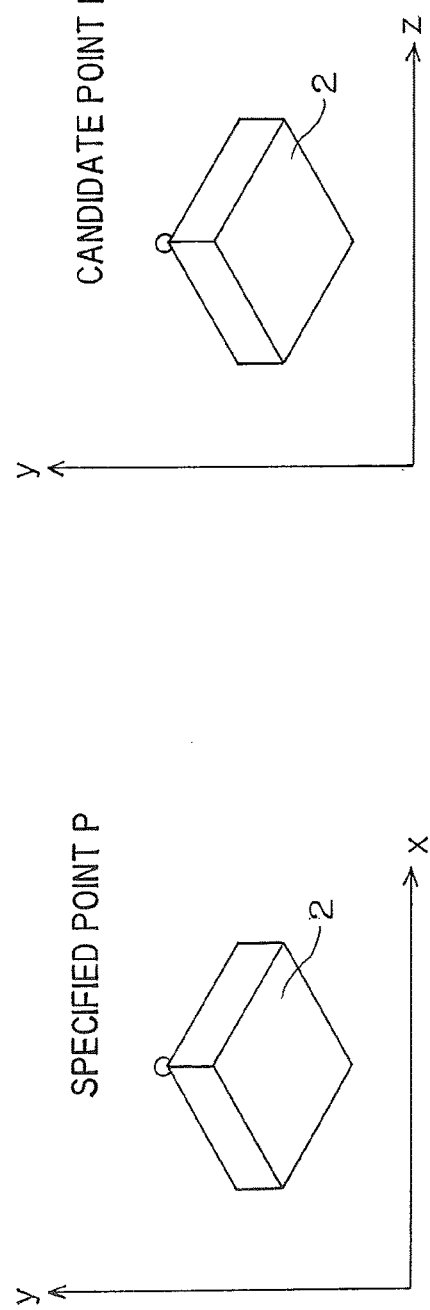
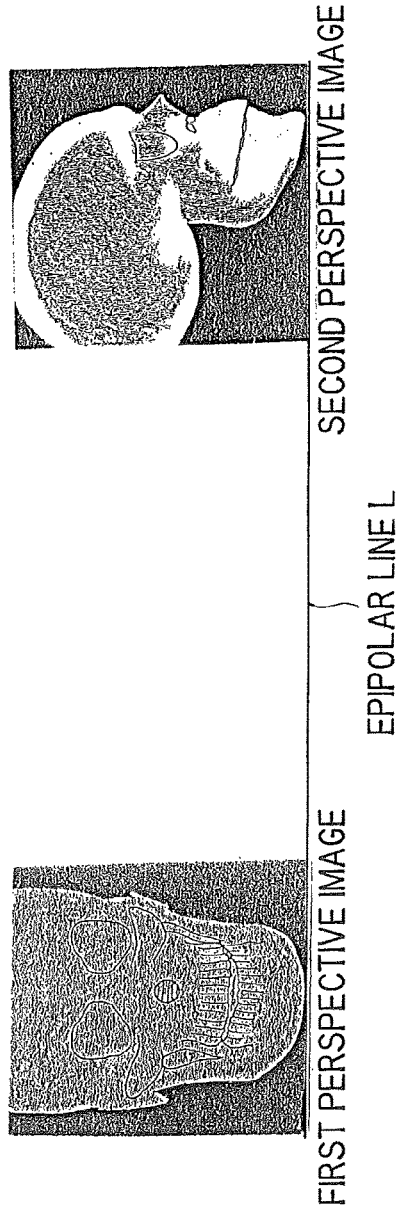
FIG. 11C
FIRST PERSPECTIVE IMAGE
EPIPOLAR LINE L
SECOND PERSPECTIVE IMAGE FIG.12A  FIG.12B
 
EXAMPLE OF HL CHARACTERISTIC PATTERN 4
FIG.13
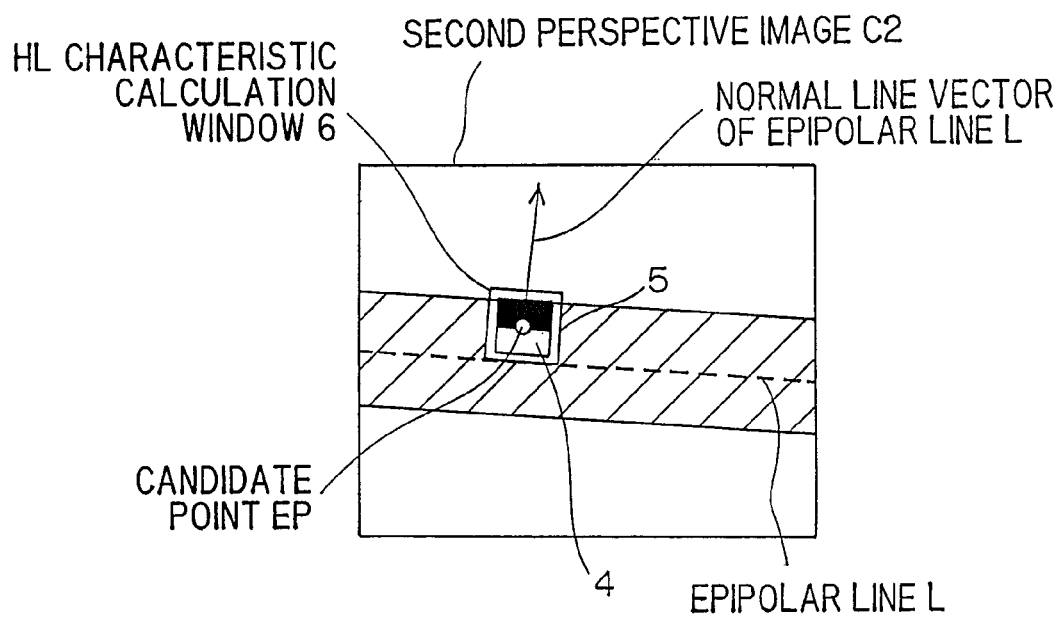
FIG.14
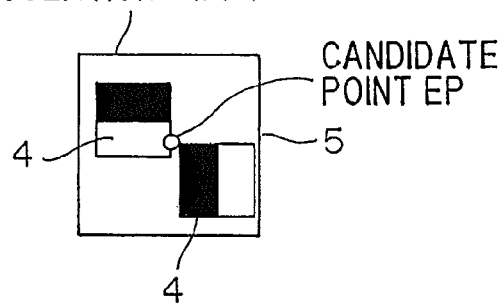

APPARATUS, METHOD AND SYSTEM FOR MEDICAL IMAGE-BASED RADIOTHERAPY PLANNING

CROSS-REFERENCE TO RELATED APPLICATIONS

This application is based upon and claims the benefit of priority from the prior Japanese Patent Application No. 2013-163425, filed on Aug. 6, 2013; the entire contents of which are incorporated herein by reference.

FIELD

Embodiments relate to a medical image processing apparatus, a medical image processing method, and a radiotherapy system.

BACKGROUND

Radiotherapy is a therapeutic approach that irradiates a lesion in a body of a patient (object under test) with a radioactive ray to destroy the lesion. At this time, normal tissues are also destroyed unless an accurate position of the lesion is irradiated with a radioactive ray.

Therefore, at the time of therapeutic planning, the position of the patient is determined first, then a perspective image in the body of the patient is photographed in advance by CT (Computed Tomography) apparatus, the position of the lesion in the body of the patient is figured out three dimensionally from the perspective image, and then a direction of irradiation and a strength of the irradiation of the radioactive ray, which reduce the probability of irradiation of the normal tissue on the basis of the position of the lesion, are determined. At the time of therapy, a new perspective image of the patient is photographed, and a medical doctor (user) inputs corresponding points on the new perspective image and the perspective image taken at the time of therapeutic planning, performs positional alignment of the patient according to the therapeutic planning, and irradiates the lesion with a radioactive ray.

However, since the therapy is repeated by a plurality of times, the positional alignment of the patient needs to be performed at every therapy. In addition, since the patient needs to maintain the same posture from the positional alignment until the termination of the irradiation of the radioactive ray, the patient suffers from a significant burden. Therefore, this positional alignment is desired to be performed accurately in a short time.

Accordingly, it is an object of the invention to provide a medical image processing apparatus, medical image processing method, and a radiotherapy system which assist a user to facilitate input of corresponding points for the positional alignment on a plurality of photographed perspective images of the object under test.

BRIEF DESCRIPTION OF THE DRAWINGS

FIGS. 5A to 5H are drawings illustrating displayed screens on a display.

FIGS. 11A and 11B are drawings illustrating projecting surfaces and FIG. 11C is a diagram illustrating relationship among the front image, the side image, and the epipolar line.

FIG. 12A and FIG. 12B are drawings illustrating examples of HL characteristic patterns.

FIG. 13 is a drawing illustrating a searching range including the epipolar line in a second perspective image.

FIG. 14 is a drawing of a HL characteristic calculation window.

DETAILED DESCRIPTION

Figure 1:
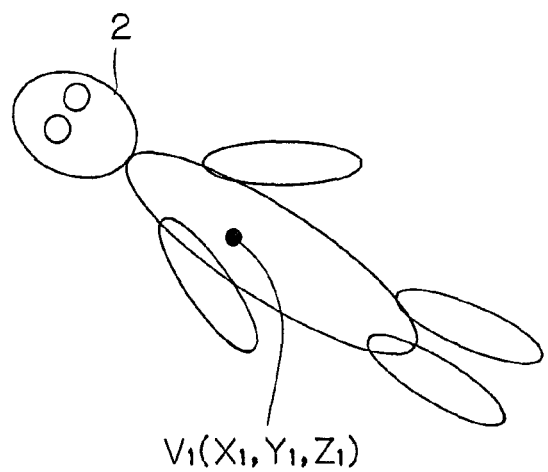
FIG. 1 is a perspective view illustrating a position of an object under test at the time of therapeutic planning.

According to embodiments, a medical image processing apparatus according to the embodiments includes: a receiver which receives target image data that is including a first perspective image and a second perspective image, photographing an object from different directions; a first acquirer which acquires positional information of a specified point on the first perspective image; a second acquirer which acquires positional information of a candidate point on the second perspective image, the candidate point corresponding to the specified point; and a generator which generates a first enlarged image obtained by enlarging a part of the first perspective image neighboring the specified point and a second enlarged image obtained by enlarging a part of the second perspective image neighboring the candidate point.

Referring now to the drawings, a medical image processing apparatus 1 of the embodiments of the invention will be described.

The medical image processing apparatus 1 of the embodiments is used in therapies on the basis of radioactive ray therapy, photon therapy, and particle radiation therapy, and is used as a positioning apparatus using perspective images obtained by photographing an object under test (patient) 2.

The term "perspective image" means images obtained by photographing in the body of an object under test 2 by using a photographing apparatus such as an X-ray photographing apparatus, a CT apparatus, or an MRI (Magnetic Resonance Imaging) apparatus.

The medical image processing apparatus 1 of the embodiments will be described with reference to FIG. 1 to FIG. 5 below.

First of all, as illustrated in FIG. 1, a user (medical doctor) lays an object under test down on a bed at the time of therapeutic planning. In this laid state, the position of a lesion of the object under test 2 in a three-dimensional space is expressed by V1 (X1, Y1, Z1). The user photographs the object under test 2 from two directions different from each other and acquires the perspective images (for example, X-ray images).

Figure 2:
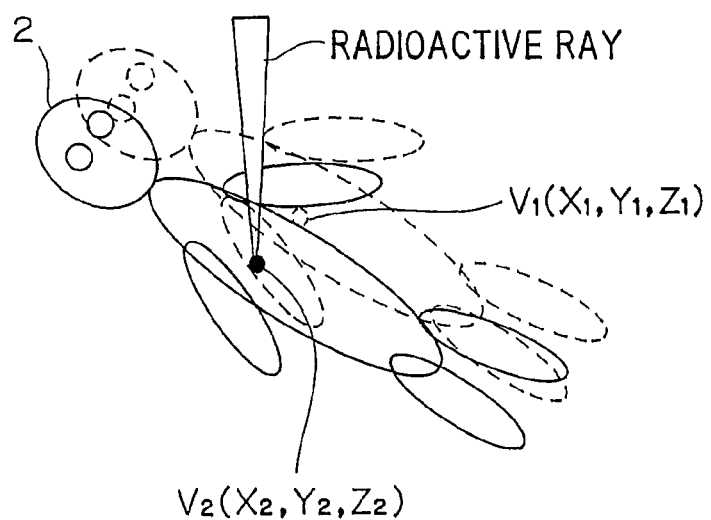
FIG. 2 is a perspective view illustrating a position of the object under treatment.

Subsequently, as illustrated in FIG. 2, the user lays the object under test 2 down on the bed again at the time of therapy. In this laid state, the position of the lesion in the body of the object under test 2 in a three-dimensional space is expressed by V2 (X2, Y2, Z2). The user photographs the object under test 2 from two directions different from each other again and acquires the perspective images (for example, X-ray images).

The user manually specifies a plurality of corresponding points in the images, which are anatomically identical, from the perspective image photographed at the time of the therapeutic planning and the perspective image photographed at the time of the therapy, obtains a displacement in position of the patient at the time immediately before the therapy from the time of the therapeutic planning and, on the basis of the obtained displacement, moves the bed to achieve the positional alignment of the object under test 2.

Figure 3:
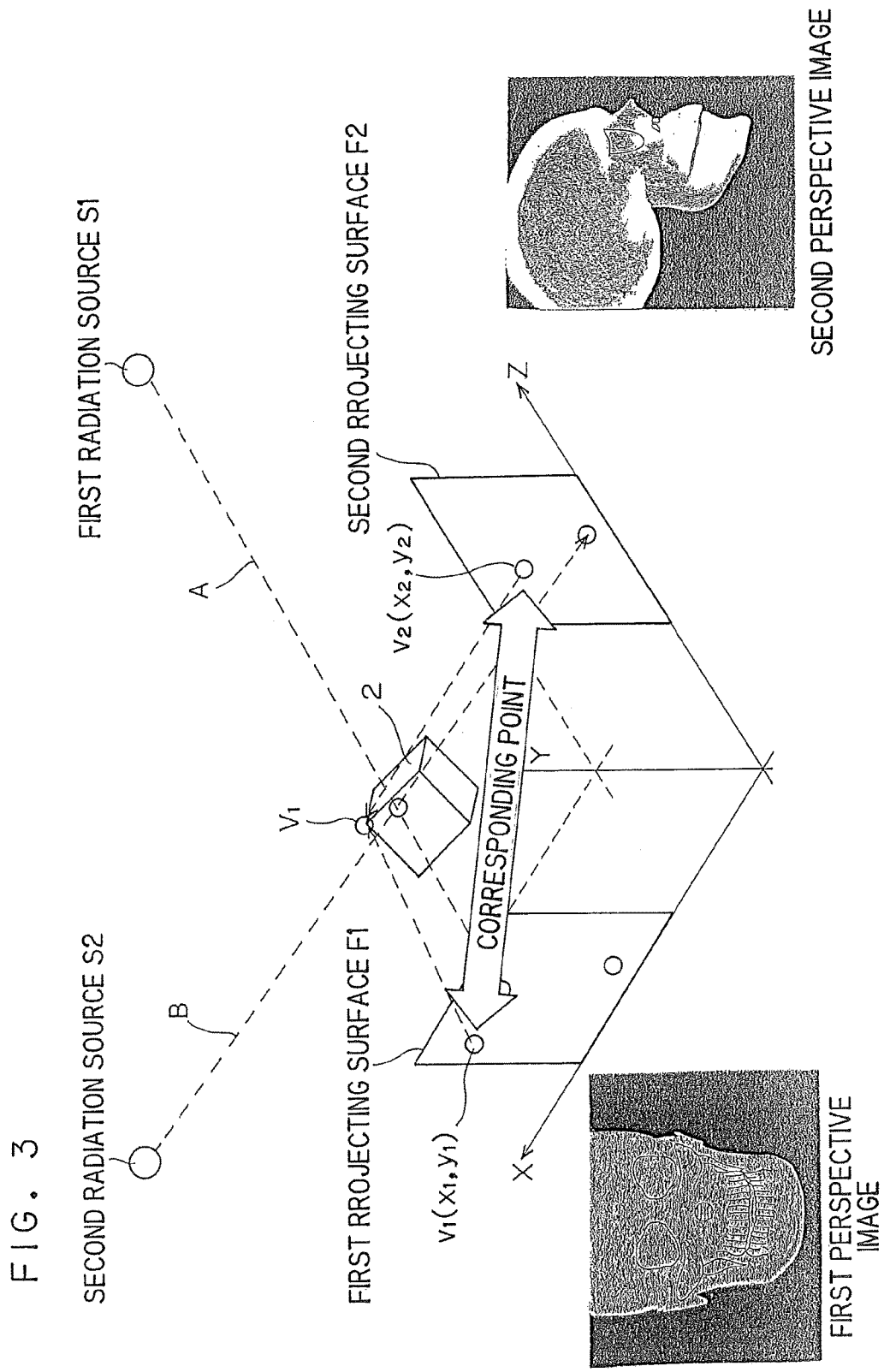
FIG. 3 is a drawing illustrating perspective images taken from two different directions.

Since the images used here are the perspective images as described above, an occluding contour such as that existing in images photographed by an optical camera does not exist, and hence a front-and-rear relationship in the body cannot be figured out easily. Therefore, the user can hardly judge the position of the lesion, which is anatomically identical, by using the perspective images of the object under test 2 photographed from two directions, that is, from the front and the side. For example, as illustrated in FIG. 3, the X-ray photographing apparatus includes a first projecting surface F1 and a second projecting surface F2 which are paired with a first radiation source S1 and a second radiation source S2, and generates a front perspective image (hereinafter referred to simply as "front image") and a side perspective image (hereinafter referred to simply as "side image") of the object under test 2. However, it is difficult to find a point v1 and a point v2, which indicate the position of a lesion V1 in the front image and the side image.

Figure 4:
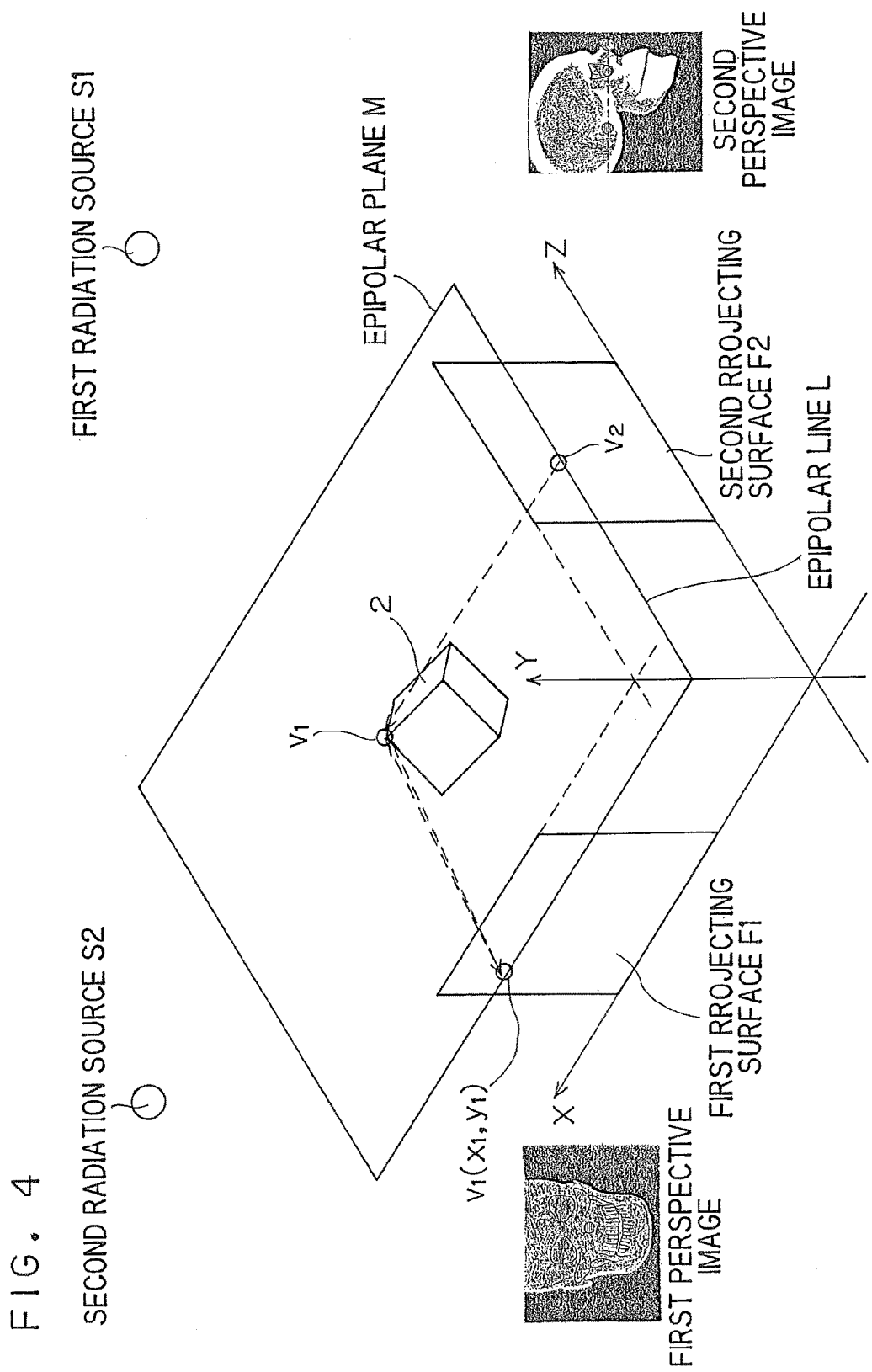
FIG. 4 is a drawing illustrating an epipolar plane and an epipolar line added to FIG. 2.

Therefore, in the method of the related art, the point v2 of the side image corresponding to the point v1 on the front image exists on the epipolar line L obtained from an epipolar constraint on the side image as illustrated in FIG. 4. Therefore, by using this geometric relationship, the epipolar line L is displayed on the side image to assist the user to input the point v2 at the anatomically identical position. However, in this method of the related art, there is a problem that even though a range that may become a candidate of the corresponding point can be narrowed down from the entire side image to the straight line L, a trouble of searching the corresponding point on the straight line L remains.

In view of the above, in the medical image processing apparatus 1 of the embodiment, when obtaining candidate points EP21, EP22, and EP23, as candidates of the corresponding point on the side image C2, which corresponds to the specified point P11 of the front image C1 at the time of therapeutic planning, the candidate points EP21, EP22, and EP23 of the side image C2 are obtained on the basis of the epipolar line L, and enlarged images E21, E22, and E23 of images of portions in the vicinity of the candidate points EP21, EP22, and EP23 are generated as illustrated in FIG. 5, whereby the user can easily input the corresponding point. In the case where the P11 is determined as the specified point, P21 corresponds to EP21, and hence the EP31 takes the same position as EP21 in the image coordinate also in the enlarged image. The points P21 and EP21 are the identical point on the same image coordinate, and hence both points are the candidate point. In the same manner, in the case of obtaining a corresponding point which corresponds to the specified point P of the front image C1 at the time of the therapeutic planning on the front image C3 at the time of the therapy, the candidate point EP of the corresponding point of the front image C3 at the time of the therapy is obtained, and an enlarged image E31 of the image of a portion in the vicinity of the candidate point EP is generated, so that the user can easily input the corresponding point. The description given above is an example only, and the specified point may be input to any one of C1 to C4.

First Embodiment

Referring now to FIG. 5 to FIG. 14, a medical image processing apparatus 1 of a first embodiment will be described below.

Figure 6:
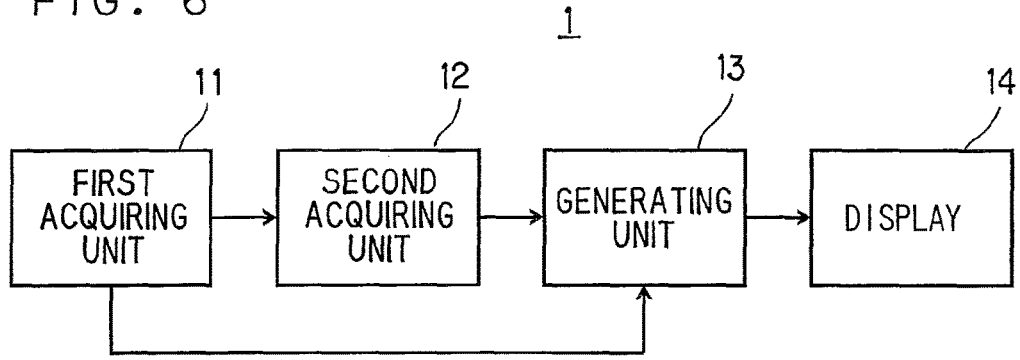
FIG. 6 is a block diagram of a medical image processing apparatus according to a first embodiment.

A configuration of a medical image processing apparatus 1 will be described on the basis of a block diagram in FIG. 6. The medical image processing apparatus 1 includes a first acquiring unit 11, a second acquiring unit 12, a generating unit 13, and a display 14.

The first acquiring unit 11 acquires a specified point P input in one perspective image which is a photograph of the object under test 2, and outputs the one perspective image and the specified point P to the second acquiring unit 12 and the generating unit 13.

The second acquiring unit 12 acquires the one perspective image from the first acquiring unit 11 and the specified point P, obtains a candidate point EP corresponding to the specified point P on another perspective image different from the one perspective image, and outputs the obtained candidate point EP to the generating unit 13.

The generating unit 13 generates an enlarged image which is an enlarged image of a portion in the vicinity of the candidate point EP in the another perspective image.

The display 14 is a display or the like, and is configured to display the one perspective image, the another perspective image, and the enlarged image side by side. An example of the image displayed by the display 14 is illustrated in FIG. 5.

In FIG. 5, reference sign "W1" denotes a window of the image of the display 14.

An image "C1" represents a first perspective image (front image of a head section of the object under test 2) photographed in a direction A of the first radiation source S1 at a time (for example, at the time of the therapeutic planning) displayed on an upper left side of the window W1.

An image "C2" represents a second perspective image (a side image of the head of the object under test 2) photographed in a direction B of the second radiation source S2 at a time 1 and displayed on a lower left side of the window W1. The display 14 does not display the epipolar line L, which will be described later, on the second perspective image C2.

An image "C3" represents a third perspective image (a front image of the head of the object under test 2) photographed in the direction A of the first radiation source S1 at a time 2 (For example, at the time of therapy) and displayed on an upper center of the window W1.

An image "C4" represents a fourth perspective image (a side image of the head of the object under test 2) photographed in the direction B of the second radiation source S2 at a time 2 and displayed on a lower center of the window W1.

An image "E11" represents an enlarged image having a center at the specified point P on the first perspective image C1 generated by the generating unit 12 and being displayed on the upper right side of the window W1.

Images "E21" to "E23" represent enlarged images having centers at the three candidate points EP on the second perspective image C2 generated by the generating unit 12 and being displayed on the lower right side of the window W1.

An image "E31" is an enlarged image having a center at a candidate point EP on the third perspective image C3 generated by the generating unit 12 and being displayed on the upper right side of the window W1.

Images "E41" to "E43" are enlarged images each having a center at each of the three candidate points EP on the fourth perspective image C4 generated by the generating unit 12 and being displayed on the lower right side of the window W1.

The medical image processing apparatus 1 performs a method of obtaining a candidate point EP on the second perspective image (side image) C2 corresponding to the specified point P on the first perspective image (front image) C1 of the object under test 2 at the time of the therapeutic planning, a method of obtaining a candidate point EP on the third perspective image (front image) C3 at the time of the therapy corresponding to the specified point P on the first perspective image (front image) C1 at the time of therapeutic planning, and a method of obtaining a candidate point EP on the fourth perspective image (side image) C4 at the time of the therapy corresponding to the specified point P of the second perspective image (side image) C2 at the time of the therapeutic planning separately, and hence these methods will be described separately as illustrated in FIG. 5. FIG. 5A is a front image at the time of therapeutic planning. FIG. 5B is a side image at the time of the therapeutic planning. FIG. 5C is the front image at the time of the therapeutic planning. FIG. 5D is a side image at the time of the therapeutic planning. FIG. 5E is an enlarged image of the front image at the time of the therapeutic planning. FIG. 5F shows enlarged images from the front image at the time of the therapeutic planning. FIG. 5G is an enlarged image of a front image at the time of therapy. FIG. 5H shows enlarged images from a side image at the time of the therapy.

First of all, a method of obtaining the candidate point EP on the second perspective image C2 corresponding to the specified point P on the first perspective image C1 of the object under test 2 at the time of the therapeutic planning will be described.

The first acquiring unit 11 acquires a plurality of perspective images from an X-ray photographing apparatus or the like, or acquires a perspective images photographed in the past from a memory device. Alternatively, a point input at the time of the therapy in the past may be memorized in the memory device and acquired therefrom.

The plurality of perspective images are perspective images of the object under test 2 photographed by irradiating the object under test 2 with an X-ray from an X-ray source of the X-ray photographing apparatus from two directions different from each other at the same time 1 (at the time of the therapeutic planning) and, in this case, correspond to the front image C1 and the side image C2. An example of the X-ray photographing apparatus 7 which photographs the perspective images from two directions different from each other is illustrated in FIG. 8.

Figure 8:
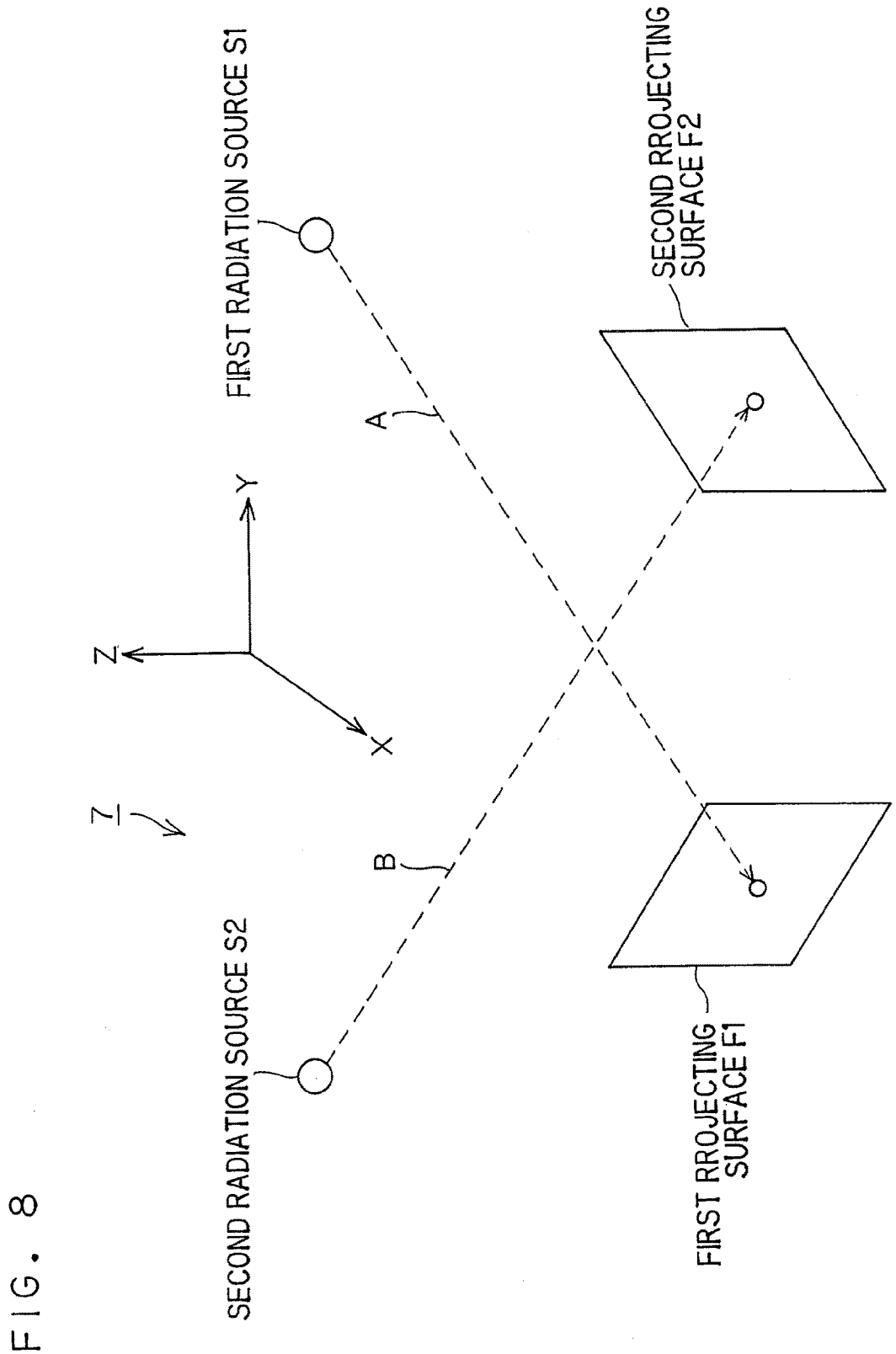
FIG. 8 is a drawing illustrating relative locations of radiation sources.

As illustrated in FIG. 8, the X-ray photographing apparatus 7 includes a first projecting surface F1 and a second projecting surface F2 that are paired with the first radiation source S1 and the second radiation source S2 respectively in a three-dimensional space on XYZ axes. The projecting surfaces F1 and F2 are each a FPD (Flat Panel Detector). An X-ray output from the first radiation source S1 passes through the interior of the object under test 2, reaches the first projecting surface F1, and generates the first perspective image (front image) C1 on the basis of energy of the passing X-ray. In the same manner, an X-ray output from the second radiation source S2 reaches the second projecting surface F2 and generates the second perspective image (side image) C2. In the X-ray photographing apparatus 7, obtained in advance are: an XYZ axes coordinate system of a three-dimensional space corrected or adjusted in respect of photographing position and defined by an apparatus system; and a transparent projection matrix for performing a coordinate conversion to and from two-dimensional coordinate systems of the respective projecting surfaces F1 and F2.

A user (for example, a medical doctor) specifies a specified point P on the first perspective image C1 displayed on the display 14, and the first acquiring unit 11 acquires v1 (x1, y1), which is a two-dimensional coordinate position (positional information) on the first projecting surface F1 relating to the specified point P. As a method of specifying the specified point P, for example, the user moves and adjusts a position of a cursor of a mouse to come to a position to be specified, on the first perspective image C1, and then presses a button of the mouse. If the display 14 is a display having a touch panel, a position touched by a finger or the like instead of the mouse may be determined as the coordinate position of the specified point P.

The second acquiring unit 12 acquires the first perspective image C1, on which the specified point P is specified, and the second perspective image C2, from the first acquiring unit 11. The second acquiring unit 12 obtains a two-dimensional position v2 (x2, y2) of the candidate point EP, which corresponds to the two-dimensional position v1 (x1, y1) of the specified point P on the first perspective image C1 (first projecting surface F1), on the second perspective image C2 (second projecting surface F2); and outputs the result to the generating unit 13. A method of obtaining the two-dimensional position v2 (x2, y2) of the candidate point EP will be described.

Figure 9:
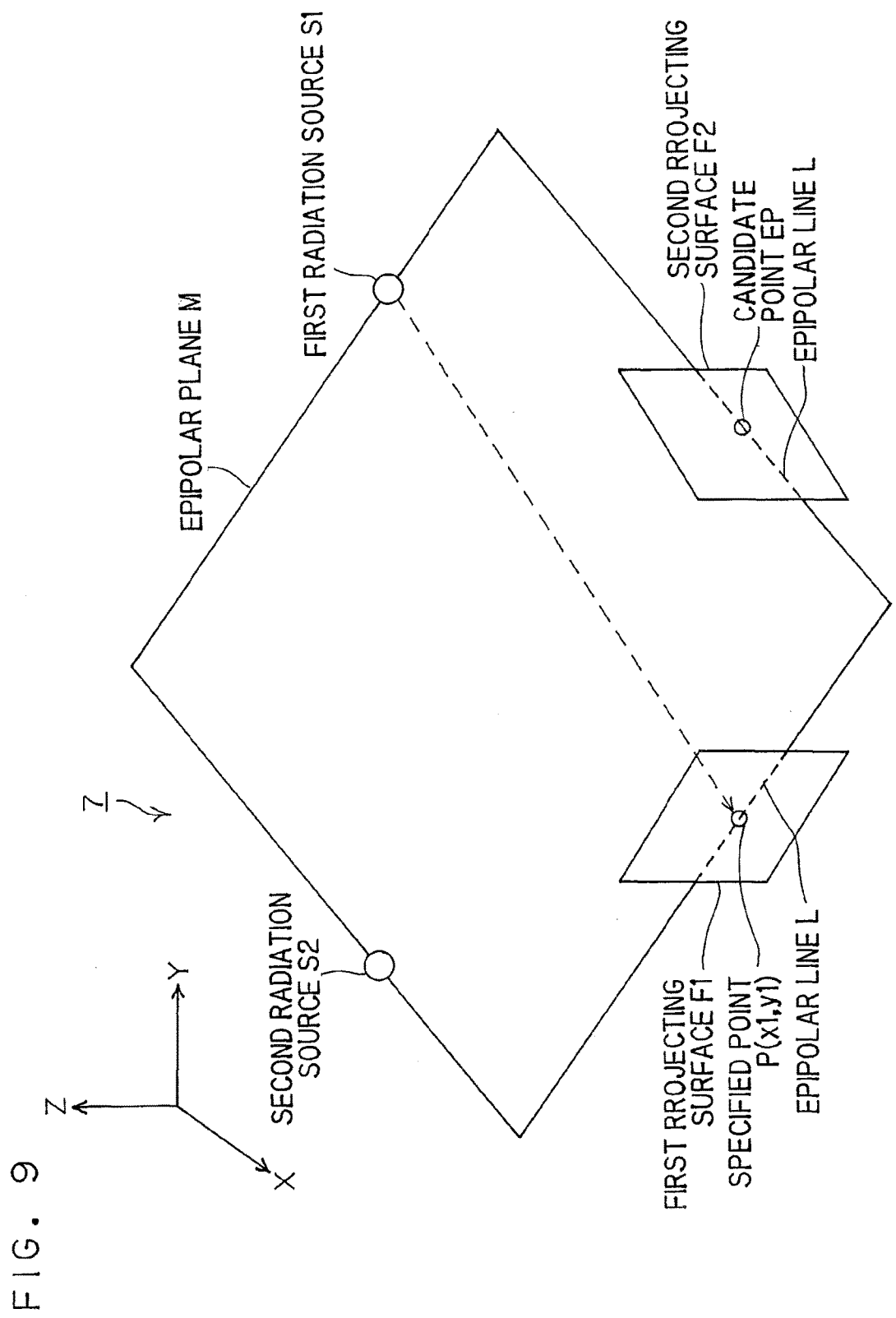
FIG. 9 is a drawing illustrating an epipolar plane added to FIG. 8.

As illustrated in FIG. 9, when a specified point P on the first perspective image C1 (first projecting surface F1) is projected on the second perspective image C2 (second projecting surface F2), a straight line L is obtained. This straight line L is acquired from an epipolar constrain. FIG. 9 illustrates an epipolar plane M of the epipolar constraint as added to the X-ray photographing apparatus 7 in FIG. 8, and the epipolar plane M is a plane including three points; the first radiation source S1, the second radiation source S2, and the specified point P on the first projecting image C1 in a three-dimensional space XYZ. The straight line L, along which the second projecting surface F2 and the epipolar plane M intersect, is identical to a straight line (epipolar line L) obtained by projecting the specified point P on the second perspective image C2. The second acquiring unit 12 obtains the epipolar line L by applying coordinate conversion to the two-dimensional coordinate v1 (x1, y1) of the specified point P on the first projecting surface F1 by use of the transparent projection matrix described above.

Figure 10:
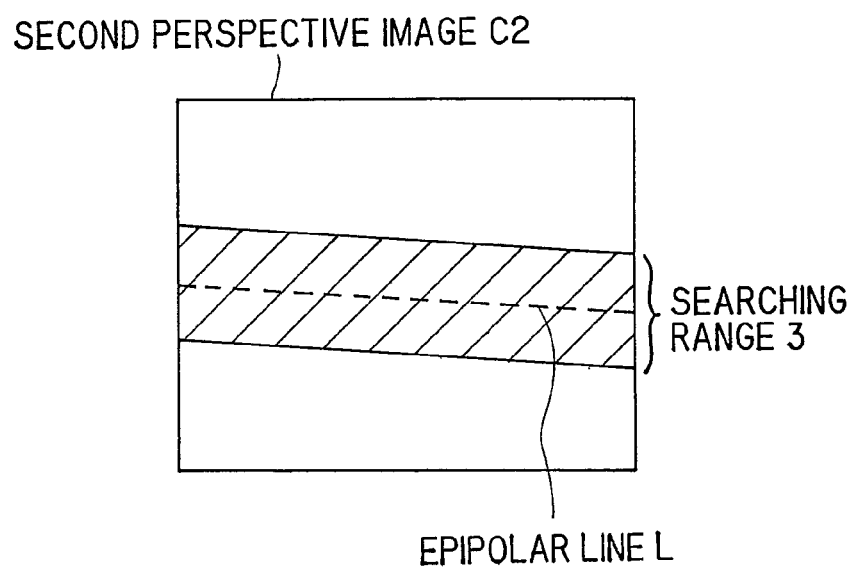
FIG. 10 is a drawing illustrating the epipolar line and a searching range.

As illustrated in FIG. 10, the second acquiring unit 12 sets a band-shaped range including the epipolar line L and having a certain width on the second perspective image C2 as the searching range 3, and finds the two-dimensional position v2(x2, y2) of the candidate point EP in the searching range 3. A method of finding the two-dimensional position v2 (x2, y2) of the candidate point EP in the searching range 3 is illustrated in FIG. 11 to FIG. 14.

The perspective image projected on the projecting surface is originally, transparent projection. However, when considering like a parallel projection, a position (apex) where the object under test 2 is in contact with the epipolar plane M is projected on the epipolar line L as a characteristic point on the first projecting surface F1 and the second projecting surface F2. For example, FIG. 11A illustrates the first projecting surface F1 and the specified point P, FIG. 11B illustrates the second projecting surface F2 and the candidate point EP, and FIG. 11C illustrates a state in which the epipolar line L is in contact with the front image C1 of a head region of the object under test 2 and with a lower end of a chin of the side view C2, and an edge of the chin (characteristic point) appears on the epipolar line L in each of the front image C1 and the side view C2.

Therefore, the second acquiring unit 12 finds the characteristic point in the searching range 3 including the epipolar line L by an edge strength, and the characteristic point is determined as the candidate point EP. The second acquiring unit 12 uses a Haar-like (hereinafter, referred to as "HL") characteristic amount as an edge strength for finding the characteristic point (edge). The term "HL characteristic amount" is a scalar amount obtained as a differential value from an average brightness in a rectangular window 5, and the value indicates the strength of the brightness gradient.

First of all, as illustrated in FIG. 12, the second acquiring unit 12 sets the rectangular window 5 having a certain size, and a HL characteristic calculation window 6 having one HL characteristic pattern 4 arranged in the rectangular window 5. The user sets a plurality of the HL characteristic patterns 4 as illustrated in FIG. 12A and FIG. 12B.

Subsequently, as illustrated in FIG. 13, the second acquiring unit 12 rotates the HL characteristic calculation window 6 having a center at a given point in the searching range 3 (this point is at an arbitrary position) in accordance with the inclination of the epipolar line L, as needed; and calculates the HL characteristic amounts at the corresponding point. Also, the HL characteristic patterns may be selected in accordance with the inclination of the epipolar line L. The second acquiring unit 12 determines a position having the largest HL characteristic amount (edge strength) from among the obtained HL characteristic amounts respectively for the points (positions) in the searching range 3, as a two-dimensional position v2 (x2, y2) of the candidate point EP. The second acquiring unit 12 may determine the position having the HL characteristic amount (edge strength) of the largest absolute value from among the obtained HL characteristic amounts, as the two-dimensional position v2 (x2, y2) of the candidate point EP. According to the method of calculating the HL characteristic amount (edge strength), the characteristic points are preferably projected as edges in a normal direction of the epipolar line L.

Subsequently, a first modification on finding the candidate point EP, in which the second acquiring unit 12 obtains the two-dimensional position v2 (x2, y2) of the candidate point EP from the searching range 3, will be described. As illustrated in FIG. 14, the second acquiring unit 12 may obtain the candidate point EP by arranging a plurality of the HL characteristic patterns 4 in the HL characteristic calculation window 6.

A second modification will be described. The second acquiring unit 12 may divide the searching range 3 into a plurality of areas each having a predetermined length of the epipolar line L, and obtain the candidate point EP in the same manner as described above in each of the divided areas. Accordingly, even in a state in which a plurality of edges having a large edge strength are concentrated, the candidate points EP may be obtained for the respective divided areas without concentrating only on the concentrated portion.

A third modification will be described. The second acquiring unit 12 obtains the HL characteristic amount in advance by using the HL characteristic calculation window 6 having a center at the specified point P of the first perspective image C1 and being rotated in accordance with the epipolar line L of the first perspective image C1. Subsequently, the second acquiring unit 12 may calculate the HL characteristic amounts for points in the searching range 3 in the second perspective image C2, and use a point most similar in the HL characteristic amount to that acquired from the specified point P, as the candidate point EP.

A fourth modification will be described. The second acquiring unit 12 may use points ranging from a point having the highest HL characteristic amount (edge strength) to a point having the Nth (N>1) largest HL characteristic amount (edge strength), as the candidate points EP. When a dynamic range of the first perspective image C1 is different from that of the second perspective image C2, the image is normalized.

A fifth modification will be described. The description has been given by using the HL characteristic amount. However, higher similarity may be decided as follows: similarity in histograms as probability distributions between two points is taken, and the smaller the Bhattacharyya distance is, the higher the similarity becomes.

A sixth modification will be described. It is also possible to search a rectangular window in which the similarity on the epipolar line L on the second perspective image C2 is the highest by using pixel values in the rectangular window of a certain size having a center at the specified point P on the first perspective image C1. A normalization cross-correlation is used for the similarities. Other image characteristic amounts may be used for the similarities. For example, the smaller the distance between vectors, the Higher the similarity is set if the similarity amount is a vector type characteristic amount.

A seventh modification will be described. The second acquiring unit 12 may modify an obtained candidate point EP to a point on the epipolar line L located at a nearest to the candidate point EP.

Subsequently, a method of obtaining a candidate point EP of the third perspective image C3 at the time of the therapy or the like, which corresponds to a specified point P of the first perspective image C1 at the time of the therapeutic planning or the like, for example, will be described.

The first acquiring unit 11 acquires the first perspective image (front image) C1 by using the X-ray photographing apparatus 7 illustrated in FIG. 8 at a certain time 1 (at the time of the therapeutic planning). The specified point P is specified by the user on the first perspective image C1 displayed on the display 14.

The second acquiring unit 12 acquires the third perspective image (front image) C3 photographed at a different time 2 (at the time of the therapy) from the substantially same direction as the first perspective image C1 by using the same X-ray photographing apparatus illustrated in FIG. 8. Unlike the perspective images (front image and the side image) from two directions different from each other, the acquired image is the perspective image photographed from the same direction, and hence there is no epipolar constraint. Therefore, a method of obtaining the candidate point EP on the third perspective image C3 corresponding to the specified point P on the first perspective image C1 will be described anew.

The rectangular window having the highest similarity is searched on the third perspective image C3 by using pixel values (for example, luminance values) within the rectangular window having a size of a certain range having a center at the specified point P on the first perspective image C1. A normalization cross-correlation is used for the similarities. Other image characteristic amounts may be used for the similarities. For example, the smaller the distance between vectors, the Higher the similarity is set if the similarity amount is a vector type characteristic amount.

A method of obtaining a candidate point EP in the fourth perspective image (side image) C4 at the time of the therapy, which corresponds to the specified point P of the second perspective image (side image) C2 at the time of the therapeutic planning is also the same as the description given above. The specified point P of the second perspective image (side image) C2 to be used at this time is the candidate point EP corresponding to the specified point P of the first perspective image (front image) C1. The specified point may be specified either on C3 or C4.

The generating unit 13 enlarges the square image of a predetermined size having a center at the candidate point EP in the second perspective image C2 and generates enlarged images E21, E22, and E23, and also enlarges square images of predetermined sizes having centers respectively at a plurality of candidate points EP within the fourth perspective image C4 and generates enlarged images E41, E42, and E43 as illustrated in FIG. 5, thereby displaying the respective candidate points EP in a superimposed manner in the display 14. The display does not display the epipolar line L on the second perspective image C2.

The generating unit 13 generates an enlarged image E11, which is an enlarged square image of a predetermined size having a center at the specified point P within the first perspective image C1 and an enlarged image E31, which is an enlarged square image of a predetermined size having a center at the candidate point EP within the third perspective image C3, and displays the specified point P and the candidate point EP in the display 14 in a superimposed manner.

The generating unit 13 resizes the square images of predetermined sizes in the first perspective image C1 to the fourth perspective image C4 and generates enlarged images. The resizing is performed by general image resizing methods such as a nearest neighbor method, a bilinear method, and a cubic convolution method.

Figure 7:
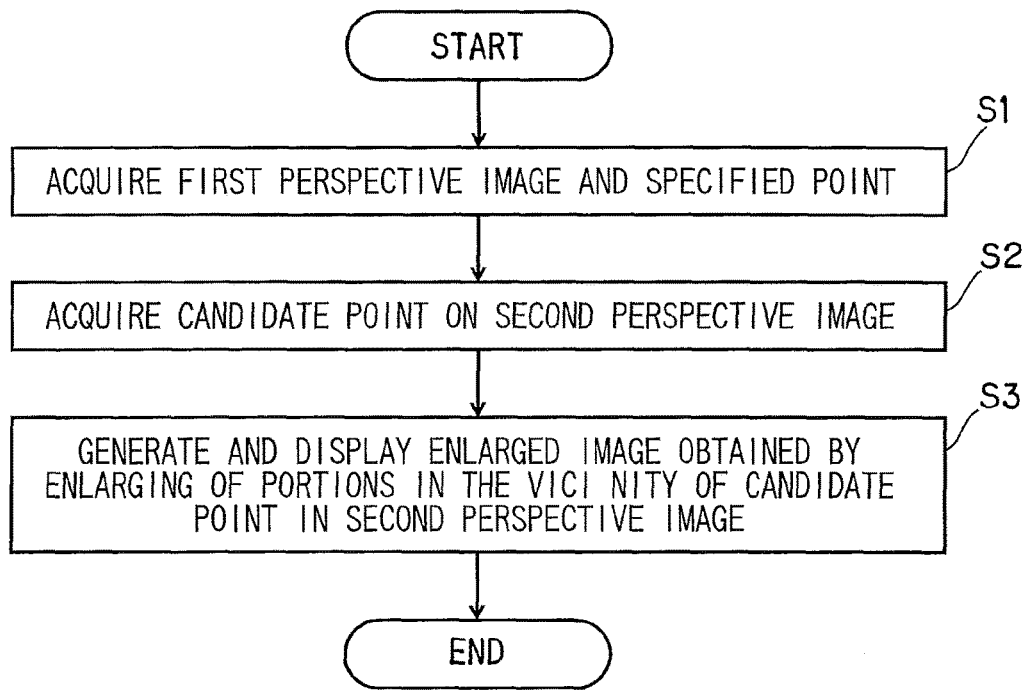
FIG. 7 is a flowchart of a medical image processing apparatus according to the first embodiment.

The process of the medical image processing apparatus 1 will be described on the basis of a flowchart illustrated in FIG. 7.

In Step S1, the first acquiring unit 11 acquires a specified point P input into the first perspective image C1.

In Step S2, the second acquiring unit 12 acquires the second perspective image C2 and the first perspective image C1 on which the specified point P is specified. Subsequently, the second acquiring unit 12 obtains a candidate point EP corresponding to the specified point P on the second perspective image C2. The second acquiring unit 12 acquires the third perspective image C3 and the first perspective image C1 on which the specified point P is specified. Subsequently, the second acquiring unit 12 obtains a candidate point EP corresponding to the specified point P on the third perspective image C3.

In Step S3, the generating unit 13 generates enlarged images E21, E22, and E23, which are enlarged images of the images in the vicinity of the candidate point EP within the second perspective image C2. Subsequently, the display 14 displays the enlarged images E21, E22, and E23 together with the candidate point EP. The generating unit 13 generates an enlarged image E31, which is an enlarged image of a portion in the vicinity of the candidate point EP within the third perspective image C3. Subsequently, the display 14 displays the enlarged image E31 together with the candidate point EP. The generating unit 13 generates enlarged images E41, E42, and E43 in the same manner, and displays the same together with the candidate point EP in the display 14. The display 14 does not display the epipolar line L on the second perspective image C2.

According to the first embodiment, the candidate points EP on the second perspective image C2 and the third perspective image C3 corresponding to the specified point P in the first perspective image C1 are obtained respectively, and images of peripheries of the candidate points EP are enlarged to generate the enlarged images E21, E22, E23, and E31 to present the same to the user, so that convenience at the time of input of the corresponding point corresponding to the specified point P is improved. In the fourth perspective image as well, the corresponding points can be input easily based on the candidate points EP of the enlarged images E41, E42, and E43.

A first modification of the first embodiment will be described. The plurality of the perspective images may be images reconstructed from a voxel data (hereinafter, referred to as DRR: Digitally Reconstructed Radiograph), which is data obtained by digitizing the inside of the object under test 2 obtained at the time of CT photographing from voxel to voxel instead of the X-ray perspective images. Since the voxel data is used, the DRR can be generated by setting view points at given positions (the first radiation source S1 and the second radiation source S2 illustrated in FIG. 8).

Alternatively, the DRR may be generated from the three-dimensional voxel data obtained from a PET (position emission tomography) apparatus, or a SPECT (single photon emission computed tomography) apparatus. In the case where the plurality of perspective images are reversed from each other between positive and negative, modification is to be performed as needed.

The plurality of perspective images may be a combination of the perspective images reconstructed from the voxel data obtained by X-ray photographing, CT-photographing, and the like.

A second modification of the first embodiment will be described. In the second acquiring unit 12, the first perspective image C1 and the third perspective image C3 are used. However, there is a case where the resolutions of the photographed images are different. In the case where the vertical and lateral lengths of one pixel in the three-dimensional space of the perspective image are known, the images are resized so that the vertical and lateral lengths of the pixel of the two perspective images become the same, and then the candidate points EP are obtained. The resizing of the image is performed by general image resizing methods such as a nearest neighbor method, a bilinear method, and a cubic convolution method as described above.

A third modification of the first embodiment will be described. The generating unit 13 may expand contrast of each enlarged image. Pixel data of each pixel which constitutes the perspective image has pixel data (luminance) in a dynamic range wider than the display dynamic range (0 to 255) of the display, which corresponds to the display 14. Therefore, the generating unit 13 expands the contrast so that 256 gradations of the display dynamic range are linearly allocated to a range from the minimum value to the maximum value of the pixel values in the enlarged image. Accordingly, the user can easily find the corresponding point from the enlarged image. The generating unit 13 may create histogram of the pixel data in the enlarged image, and performs histogram equalization to allocate the non-linear gradient.

A fourth modification of the first embodiment will be described. The generating unit 13 may display an enlarged differential image of the enlarged image E11 of the first perspective image C1 and the enlarged image E21 of the second perspective image C2 when displaying the enlarged image E21. The enlarged differential image may be generated from the differential of luminance values of the pixels each in the enlarged image E11 and the differential of luminance values of the respective pixels in the enlarged image E21. Accordingly, convenience at the time when the user input the point corresponding to the specified point P is improved. In the case where the dynamic ranges of the pixel data of the enlarged image E11 and the enlarged image E22 are different, both of the images are normalized (the range of the normalized data is 0 to 1) to obtain the differential (the normalized differential data is −1 to 1), and 256 gradations of the display dynamic range are allocated.

A fifth modification of the first embodiment will be described. The user may directly point out the candidate point EP on the second perspective image C2 by a mouse or the like, and store the pointed positions of the second perspective image C2 and the candidate point EP by the second acquiring unit 12.

A sixth modification of the first embodiment will be described. In the case where the read perspective image already has a point which has been specified at the previous therapy, the point may be stored and reused as the specified point.

A modification 7 of the first embodiment will be described. In the above description, when the generating unit 13 generates the enlarged image, the enlarged image is centered at the candidate point or the specified point, however, the invention is not limited thereto, if the candidate point or the specified point is included in the enlarged image, the generating unit 13 may generate an enlarged image with these points located at positions other than the center.

Second Embodiment

Referring now to FIG. 15 to FIG. 23, the medical image processing apparatus 1 according to a second embodiment will be described.

Figure 15:
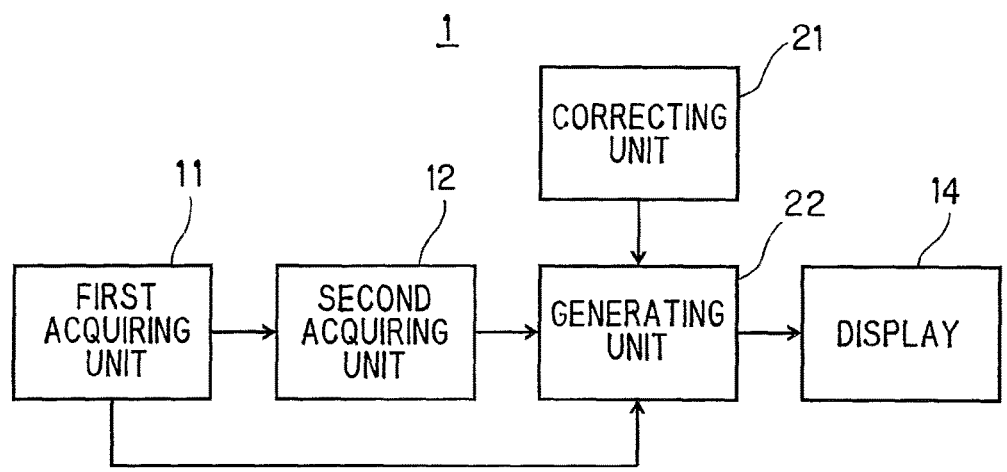
FIG. 15 is a block diagram of a medical image processing apparatus according to the second embodiment.

The medical image processing apparatus 1 according to the second embodiment will be described on the basis of the block diagram illustrated in FIG. 15. The medical image processing apparatus 1 includes the first acquiring unit 11, the second acquiring unit 12, a correcting unit 21, the generating unit 22, and the display 14. The second embodiment is different from the first embodiment in that the correcting unit 21 is added and in the process of the generating unit 22. Therefore, only the different configuration and the operation are described, and description of the configuration and the operation which are the same as those in the first embodiment will be omitted.

Figure 17:
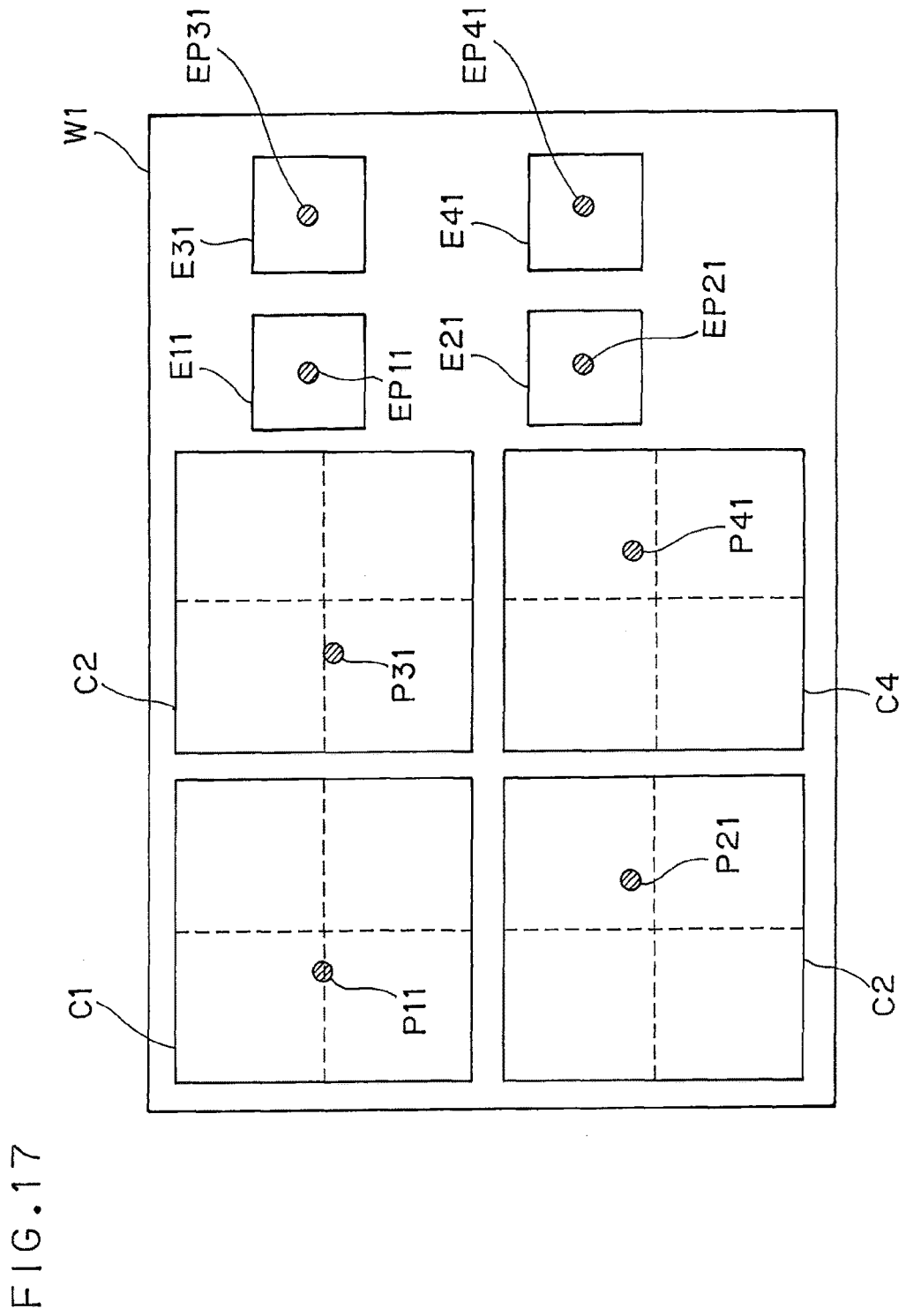
FIG. 17 is a drawing of a display screen of a display of the second embodiment.

The display 14 displays the first perspective image C1, the second perspective image C2, the third perspective image C3, the fourth perspective image C4, the enlarged image E11, the enlarged image E21, the enlarged image E31, the enlarged image E41, the specified point P, and the candidate point EP as illustrated in FIG. 17 in the same manner as the display 14 of the first embodiment. The display 14 does not display anything if the enlarged images E11, E21, E31, and E41 are not generated.

In the following description, the specified point P and the candidate point EP are not discriminated, and are expressed simply as "point".

The generating unit 22 acquires the candidate points EP from the first acquiring unit 11 and the second acquiring unit 12, generates an enlarged image, and displays the same in the display 14 in the same manner as the generating unit 13 of the first embodiment. The generating unit 22 acquires coordinate of the specified point P and the candidate point EP corrected by the correcting unit 21, which will be described later, and generates the enlarged image and displays the same in the display 14.

The user corrects the positions of the specified point P and the candidate point EP displayed in the display 14 by using an interface such as a mouse, and the correcting unit 21 acquires the coordinates of the corrected points and outputs the coordinates of the corrected points to the generating unit 22. In the case where the mouse pointer is on the enlarged images E11, E21, E31, and E41 displayed on the display 14, and the correcting unit 21 does not select a point, an enlargement factor is changed by moving the mouse wheel.

The correction of the point by the correcting unit 21 is achieved by the user, by clicking at a position near the point to select the point with a mouse, and dragging the point to move the position. For example, when the user selects a point P11 on the first perspective image C1, the correcting unit 21 changes successively the positional coordinate of the point P11 on the first perspective image C1, and outputs the coordinates to the generating unit 22 while drawing the points. The generating unit 22 changes the enlarged image E11 into an enlarged image E11 having a center at the point P11 or its coordinates, at that time point. At this time, since the drawing position of the point EP11 is located at the center of the enlarged image E11, there is no more change in the drawing position. Also, the correcting unit 21 does not change the magnitude of the display range of the enlarged image E11.

When the user selects and corrects the point EP11 on the enlarged image E11, the correcting unit 21 does not output the coordinates of the point EP11, which is changed successively, to the generating unit 22, and changes only the drawing positions of the point EP11 on the enlarged image E11 and the point P11 on the first perspective image C1 successively.

The correcting unit 21 changes the enlarged image in the same manner also in the case where the point EP21, the point EP31, and the point EP41 are selected.

Figure 16:
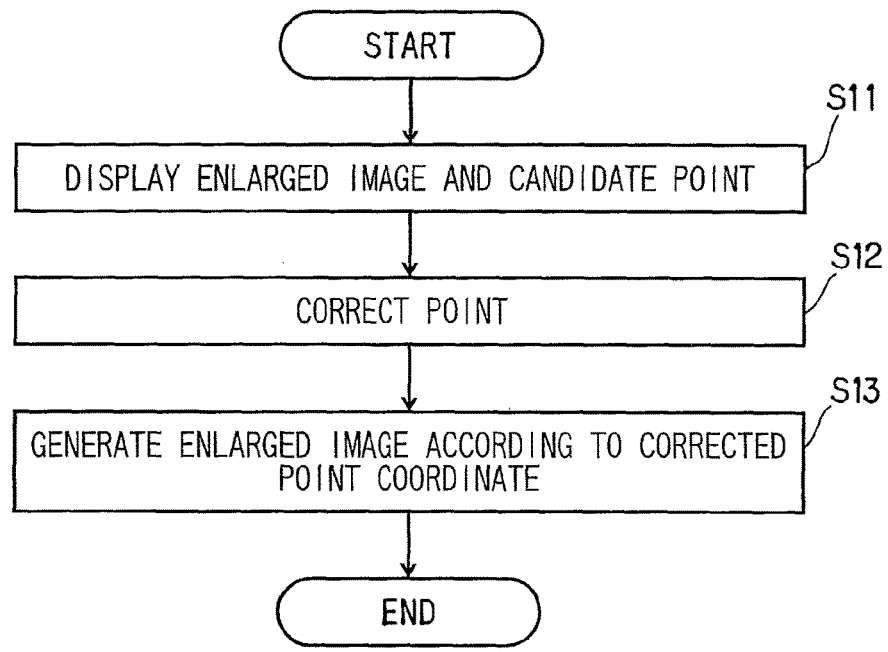
FIG. 16 is a flowchart of a medical image processing apparatus according to the second embodiment.

The process of the medical image processing apparatus 1 will be described on the basis of the flowchart illustrated in FIG. 16. The flowchart is started from the time point when the enlarged image is generated in the first embodiment.

In Step S11, the generating unit 22 displays an enlarged image and a candidate point EP in the display 14 as illustrated in FIG. 17.

In Step S12, the correcting unit 21 corrects the coordinate of the specified point P or the candidate point EP selected and corrected by the user.

In Step S13, the generating unit 22 generates an enlarged image according to the coordinate of the corrected point, and displays again in the display 14.

According to the second embodiment, since the user can easily correct the points on the image, input of the corresponding point can be performed further easily.

Figure 18:
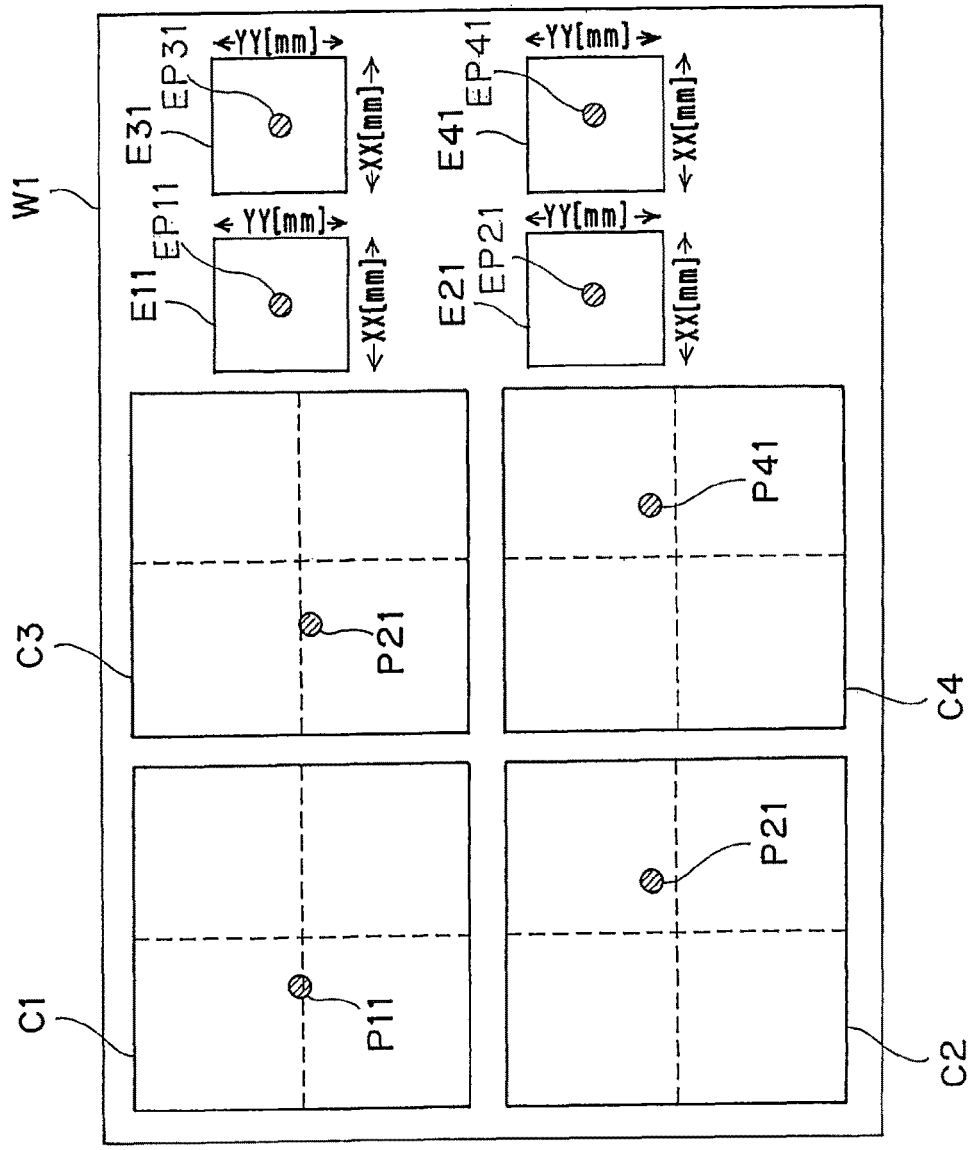
FIG. 18 is a drawing of a display screen of a display of a first modification.

A first modification of the second embodiment will be described. As illustrated in FIG. 18, the horizontal length and vertical length in the three-dimensional space of the display range of the enlarged image may be displayed respectively on the lower side and on the right side of each of the enlarged images E11, E21, E31, and E41, in accordance with the magnification factors of the enlarged images E11, E21, E31, and E41.

Figure 19:
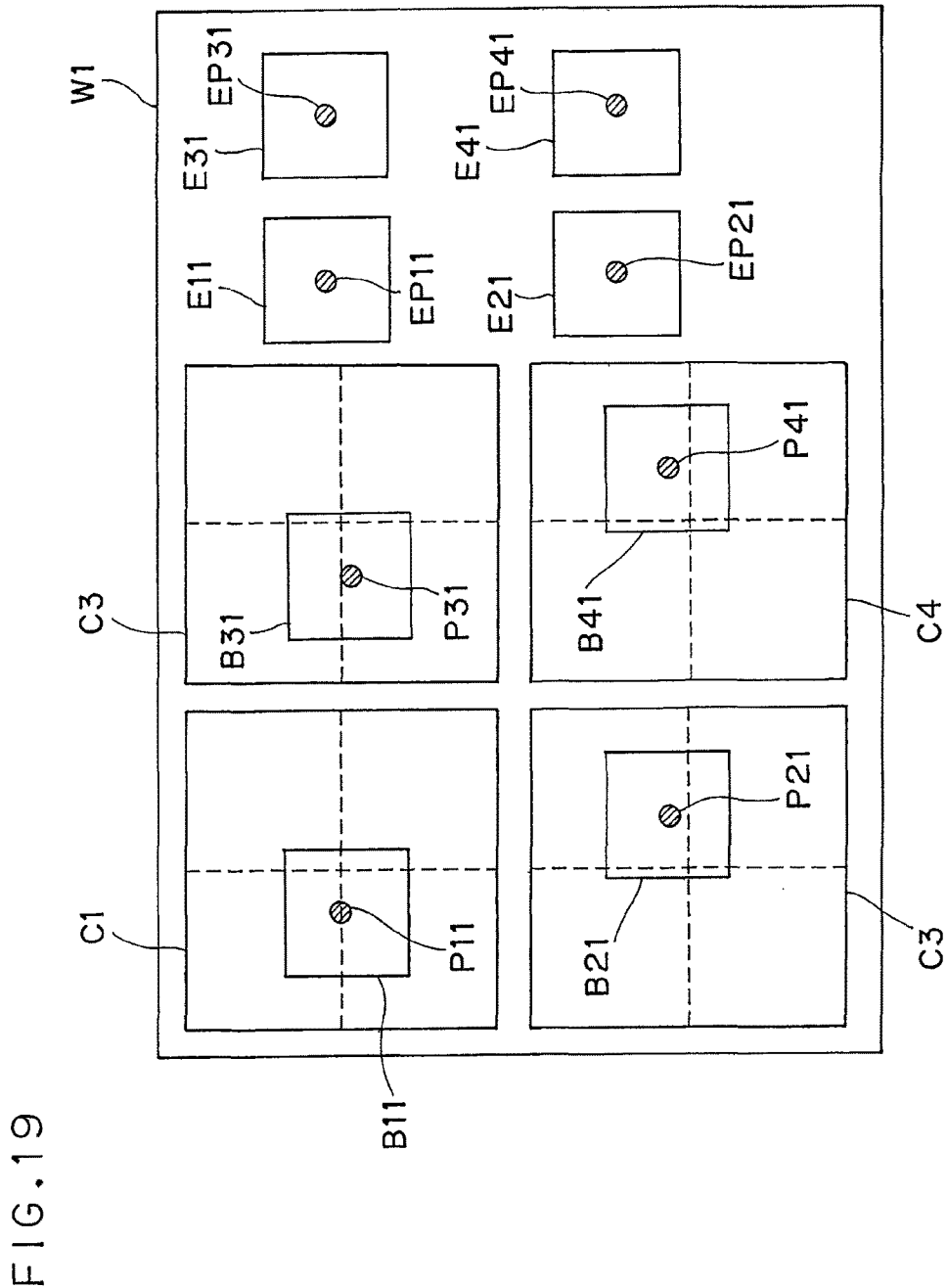
FIG. 19 is a drawing of a display screen of a display of a second modification.

A second modification of the second embodiment will be described. As illustrated in FIG. 19, a part or a range of the first perspective image C1, which is displayed in the enlarged image E11 may be indicated by a rectangular frame B11 on the first perspective image C1. The same applies to the second perspective image C2, the third perspective image C3, and the fourth perspective image C4.

Figure 20:
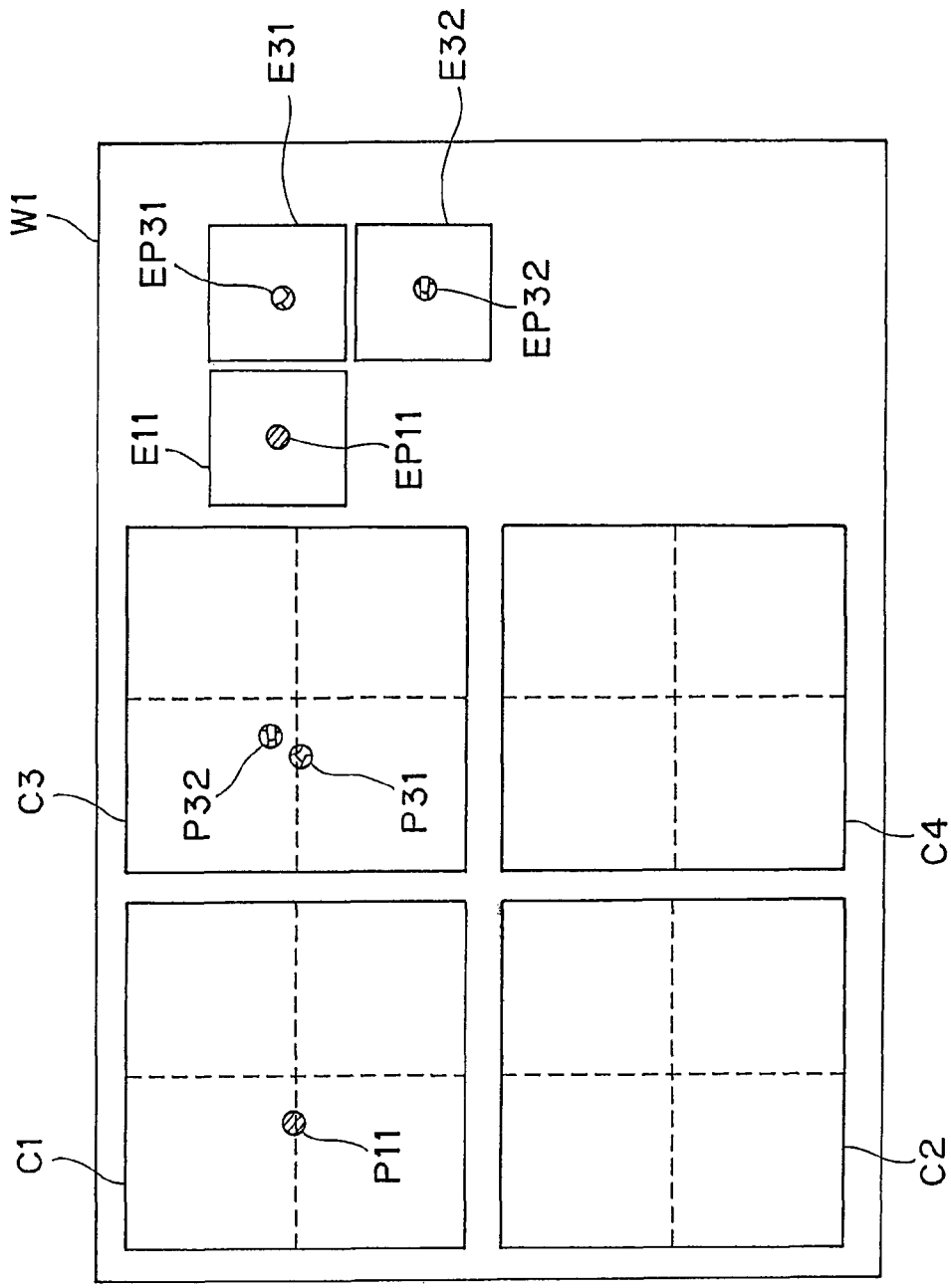
FIG. 20 is a drawing of a display screen of a display of a third modification.

A third modification of the second embodiment will be described. In this modification, manner of displaying on the display 14 will be described in the case where there are a plurality of the candidate points EP. As illustrated in FIG. 20, the display 14 shows a plurality of candidate points EP31 and EP32 on the third perspective image C3 in relation to a specified point P11 of the first perspective image C1. At this time, the user clicks one of the enlarged images E31 and E32, and selects one of the plurality of candidate points EP. When the selection is completed, the display goes to a screen illustrated to FIG. 17. In FIG. 20, since a color coding display is not possible in the drawings, differentiated hatching lines are employed.

The scales as illustrated in FIG. 18 may be displayed on the lower side and the right side of the enlarged images E11, E21, and E13, respectively (not illustrated).

Figure 21:
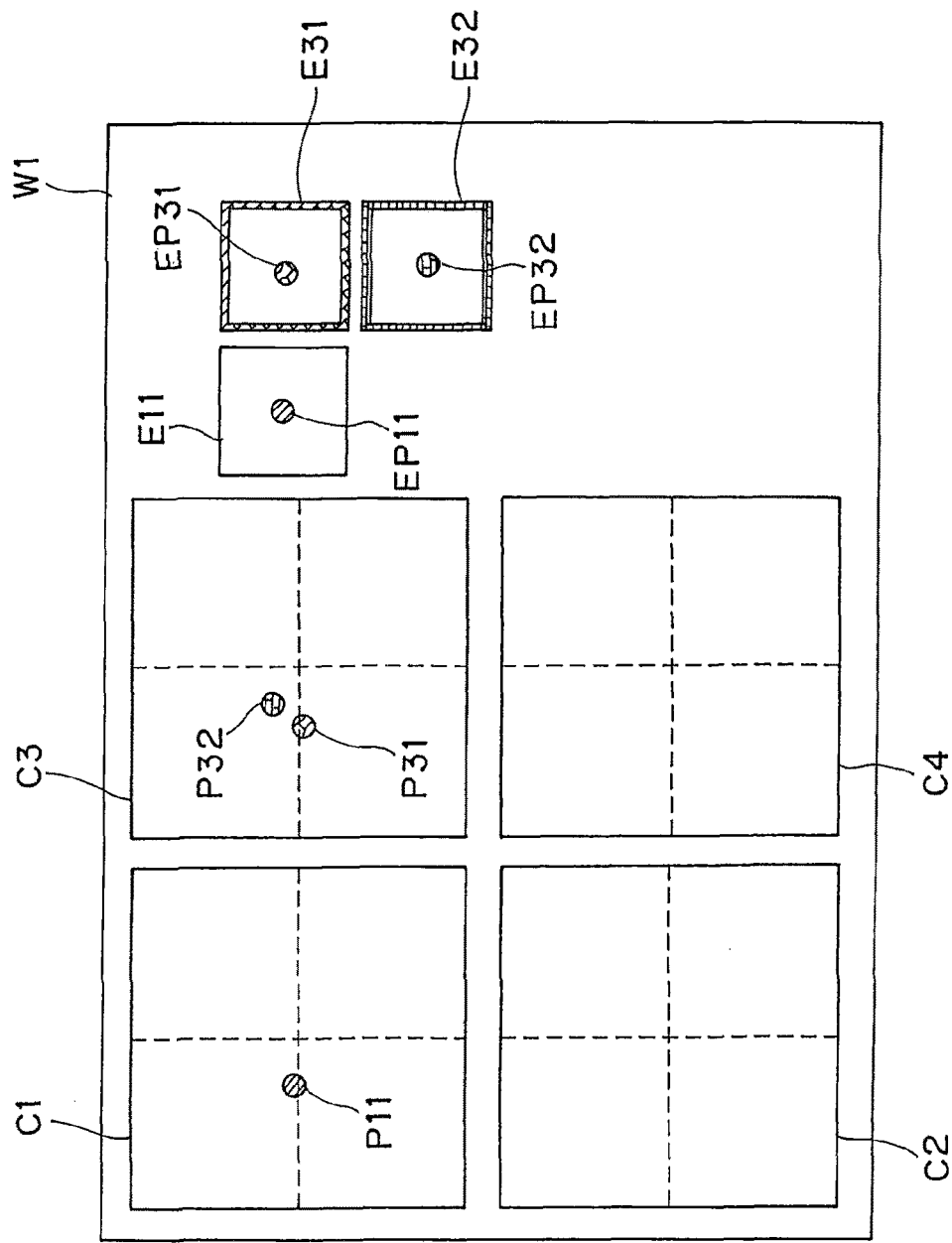
FIG. 21 is another example of the display screen of the display of the third modification.

If there is a plurality of candidate points EP, the respective points P31 and P32 may be color coded and displayed as indicated in FIG. 21. It is also possible to provide the frames in the same colors as those used for indicating the points, on fringes of the enlarged images E31 and E32 corresponding to the respective candidate points EP. In FIG. 21, since a color coding display is not possible in the drawings, differentiated hatching lines are employed.

Figure 22:
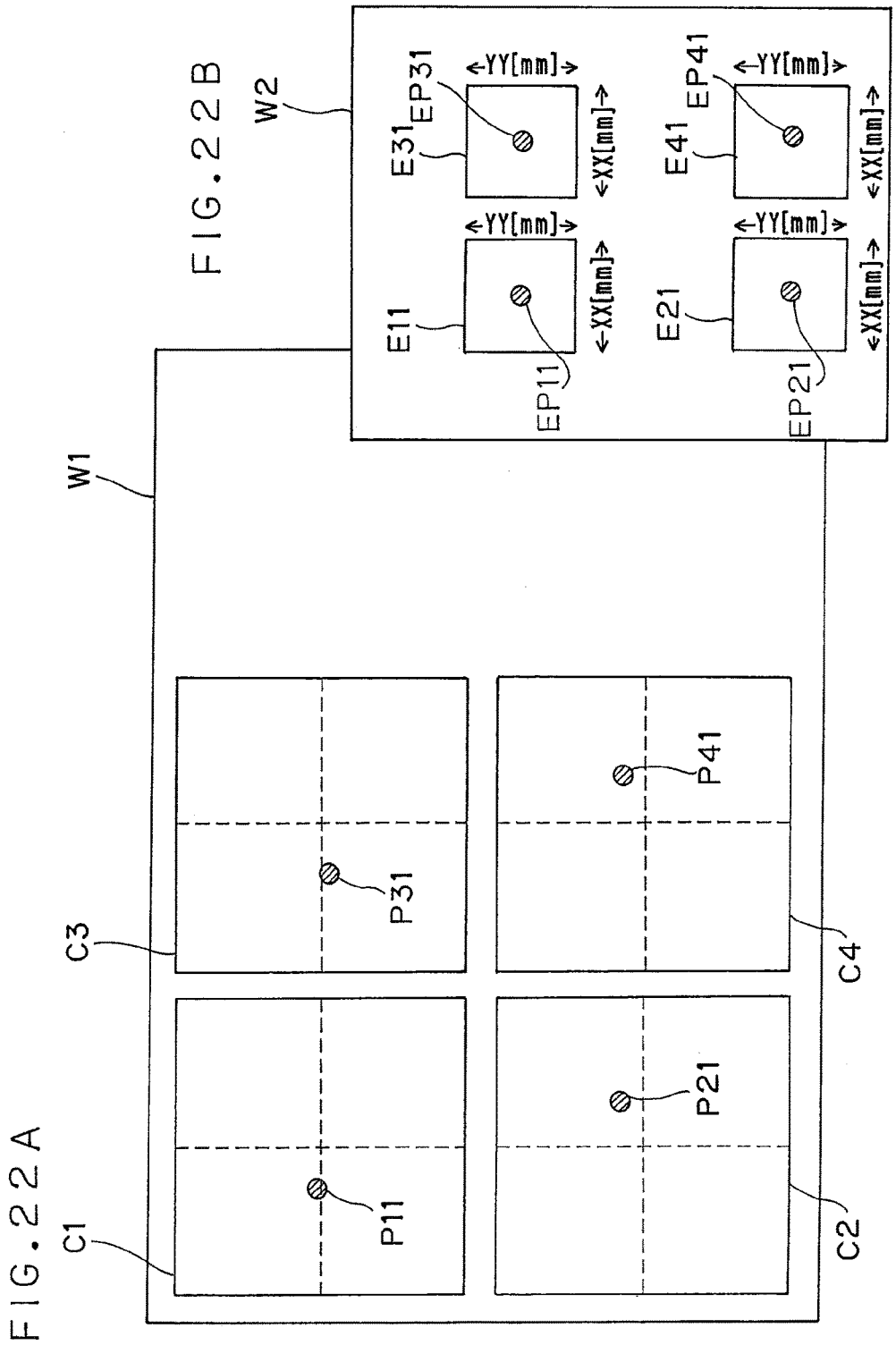
FIGS. 22A and 22B are drawings of a display screen of a display of a fourth modification.
Figure 23:
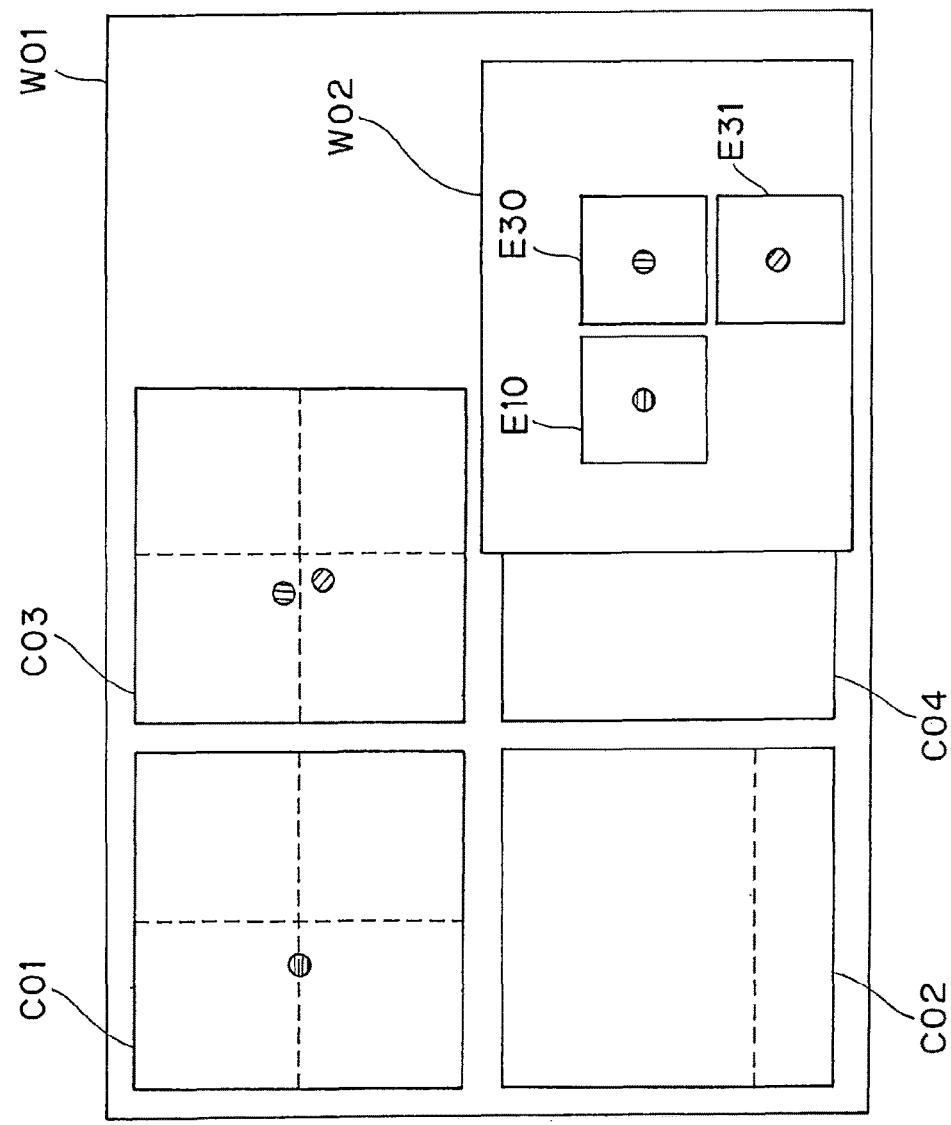
FIG. 23 is another example of the display screen of the display of the fourth modification.

A fourth modification of the second embodiment will be described. In the above-described embodiments, the enlarged images E11, E21, E31, and E41 are arranged on the right side of the window W1. However, these may be arranged on the left side of the window W1 (not illustrated). Alternatively, as illustrated in FIG. 22 and FIG. 23, the enlarged images may be displayed with floating windows W2 and W02.

A fifth modification of the second embodiment will be described. Tools used for selection and transfer of points by the correcting unit 21 are not limited to the mouse and a keyboard and a touch pen may be employed and, if the display has a touch panel, a flick input by the user is also applicable.

In the respective embodiments described above, description has been given with the perspective images which are obtained by photographing the first perspective image C1 and the second perspective image C2 at the time of the therapeutic planning and photographing the third perspective image C3 and the fourth perspective image C4 at the time of the therapy. However, the invention is not limited thereto, and the perspective images may be obtained by photographing the first perspective image C1 and the second perspective image C2 at the time of the first therapy, and photographing the third perspective image C3 and the fourth perspective image C4 at the time of the second therapy. In other words, what is essential is that the first perspective image C1 and the second perspective image C2 are photographed at the substantially same time and the third perspective image C3 and the fourth perspective image C4 are photographed at the substantially same time, and the first perspective image C1 and the second perspective image C2 are photographed at different time or at the substantially same time as the third perspective image C3 and the fourth perspective image C4.

In the above-described embodiment, the front image and the side image of the object under test 2 are used as the perspective images photographed from the two different directions. However, this is an example only, and the other perspective images of the object under test 2 from the two different directions are also applicable.

In the above-described embodiment, the head region of the patient has been described as the object under test 2. However, the invention is not limited thereto, other portions such as a breast region or an abdominal region are also applicable.

The medical image processing apparatus 1 may be implemented by using, for example, a general purpose computer apparatus as a basic hardware. In other words, the first acquiring unit 11, the second acquiring unit 12, the generating unit 13, the correcting unit 21, and the generating unit 22 are implemented by causing a processor mounted on the above-described computer apparatus to execute a program. At this time, the medical image processing apparatus 1 may be implemented by installing the above-described problem in the computer apparatus in advance, or may be implemented by storing the same in a storage medium such as a CD-ROM or an USB memory, distributing the above-described program via network, and installing the distributed program in the computer apparatus as needed. The storage device for the perspective images or the like in the medical image processing apparatus 1 may be implemented by using integrated or external memory, or a hard disk, or storage medium such as a CD-R, a CD-RW, a DVD-RAM, a DVD-R, as needed.

Figure 24:
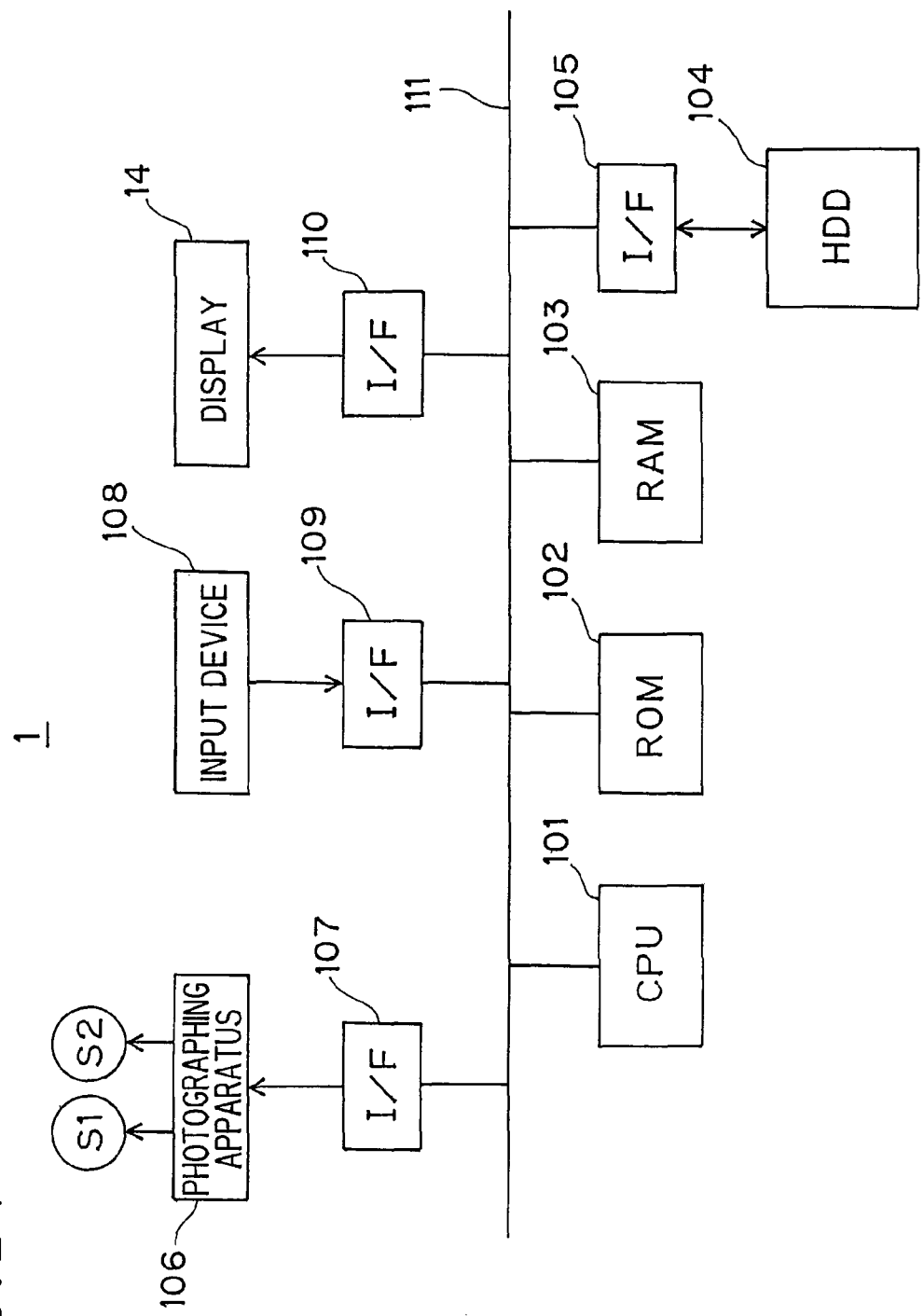
FIG. 24 is a block diagram showing an example of hardware construction of the medical image processing apparatus.

FIG. 24 is a block diagram showing an example of hardware construction of the medical image processing apparatus. As shown herein, the medical image processing apparatus 1 comprises: a CPU (central processing unit) 101; an ROM (Read Only Memory) 102 storing the program for measurement, and the like; RAM (Random Access Memory) 103; HDD (hard disk drive) 104; I/F 105, which is an interface for the HDD 104; a photographing apparatus 106 having radiation sources S1 and S2 such as X-ray photographing apparatus, a CT scanner and an MRI (Magnetic Resonance Imaging) apparatus; I/F 107, which is an interface for the photographing apparatus; an input device 108 such as a mouse or a keyboard; I/F 109, which is an interface for the input device; a display 14 such as a visual display unit; I/F 110, which is an interface for the display 14; a computer bus 111. Thus, the medical image processing apparatus 1 utilizes a hardware construction of common computers. The CPU 101, the ROM 102, the RAM 103, the I/Fs 105, 107, 109 and 110 are connected with each other, through the computer bus 111.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An apparatus for medical image-based radiotherapy planning, comprising:
   a processor; and
   a memory configured to store processor-executable instructions which, when executed by the processor, cause the processor to at least:
   receive a first perspective image and a second perspective image, obtained by photographing an object from different directions;
   acquire positional information of a specified point on the first perspective image;
   search, in a searching range including an epipolar line on the second perspective image, for a candidate point based on a Haar-like characteristic amount, the candidate point corresponding to the specified point, the epipolar line corresponding to the specified point;
   calculate the Haar-like characteristic amount of a given point in the searching range by rotating a Haar-like characteristic calculation window having a center at a given position in accordance with an inclination of the epipolar line; and
   generate a first enlarged image by enlarging a part of the first perspective image neighboring the specified point, a second enlarged image by enlarging a part of the second perspective image neighboring the candidate point, and a differential image indicating differences between luminance values of pixels in the first enlarged image and luminance values of pixels in the second enlarged image.

2. The apparatus according to claim 1, wherein the instructions cause the processor to generate the second enlarged image when the candidate point exists on the second perspective image.

3. The apparatus according to claim 1, wherein the instructions cause the processor to determine a point having a highest Haar-like characteristic amount as the candidate point.

4. The apparatus according to claim 1, wherein the instructions cause the processor to determine points from a point having a highest Haar-like characteristic amount to a point having an Nth highest Haar-like characteristic amount as candidate points, wherein N>1.

5. The apparatus according to claim 1, wherein the instructions cause the processor to divide a searching range into divided areas, and search for candidate points in each divided area.

6. The apparatus according to claim 1, wherein the instructions cause the processor to generate the first and second enlarged images superimposed on the candidate point.

7. The apparatus according to claim 6, wherein the instructions cause the processor to process a received instruction to move the candidate point on the second enlarged image.

8. The apparatus according to claim 7, wherein the instructions cause the processor to not change a size of a display range of the first and second enlarged images when the candidate point is moved.

9. The apparatus according to claim 6, wherein the instructions cause the processor to move the candidate point on the second enlarged image so that a corrected candidate point moves onto the epipolar line.

10. The apparatus according to claim 1, wherein the instructions cause the processor to determine a point at which the Haar-like characteristic amount is a maximum as a position of the candidate point.

11. The apparatus according to claim 1, wherein the instructions cause the processor to resize the second perspective image and generate the second enlarged image.

12. The apparatus according to claim 1, further comprising a display, wherein
   the display displays the first perspective image, the second perspective image, and first and second enlarged images on a screen.

13. A method for medical image-based radiotherapy planning, comprising:
   receiving a first perspective image and a second perspective image, obtained by photographing an object from different directions;
   acquiring positional information of a specified point on the first perspective image;
   searching, in a searching range including an epipolar line on the second perspective image, for a candidate point based on a Haar-like characteristic amount, the candidate point corresponding to the specified point, the epipolar line corresponding to the specified point;
   calculating the Haar-like characteristic amount of a given point in the searching range by rotating a Haar-like characteristic calculation window having a center at a given position in accordance with an inclination of the epipolar line; and
   generating a first enlarged image by enlarging a part of the first perspective image neighboring the specified point, a second enlarged image by enlarging a part of the second perspective image neighboring the candidate point, and a differential image indicating differences between luminance values of pixels in the first enlarged image and luminance values of pixels in the second enlarged image.

14. A system for medical image-based radiotherapy planning, comprising:
   a memory device for storing computer readable program code; and
   a processor in communication with the memory device, the processor being operative with the computer readable program code to at least:
   receive a first perspective image and a second perspective image, obtained by photographing an object from different directions;
   acquire positional information of a specified point on the first perspective image;
   search, in a searching range including an epipolar line on the second perspective image, for a candidate point based on a Haar-like characteristic amount, the candidate point corresponding to the specified point, the epipolar line corresponding to the specified point;
   calculate the Haar-like characteristic amount of a given point in the searching range by rotating a Haar-like characteristic calculation window having a center at a given position in accordance with an inclination of the epipolar line; and generate a first enlarged image by enlarging a part of the first perspective image neighboring the specified point, a second enlarged image by enlarging a part of the second perspective image neighboring the candidate point, and a differential image indicating differences between luminance values of pixels in the first enlarged image and luminance values of pixels in the second enlarged image.

15. The system according to claim 14, further comprising a radiation source which emits radiation directed at a target in the object.

* * * * *